US011464851B2

(12) United States Patent
Papasotiriou

(10) Patent No.: US 11,464,851 B2
(45) Date of Patent: Oct. 11, 2022

(54) SARS-COV-2 VACCINES

(71) Applicant: R.G.C.C. Holdings AG, Zug (CH)

(72) Inventor: Ioannis Papasotiriou, Oberageri (CH)

(73) Assignee: R.G.C.C. Holdings AG, Zug (CH)

( * ) Notice: Subject to any disclaimer, the term of this patent is extended or adjusted under 35 U.S.C. 154(b) by 0 days.

(21) Appl. No.: 17/401,584

(22) Filed: Aug. 13, 2021

(65) Prior Publication Data

US 2022/0111037 A1     Apr. 14, 2022

Related U.S. Application Data

(63) Continuation of application No. 17/349,462, filed on Jun. 16, 2021, now abandoned.

(30) Foreign Application Priority Data

Oct. 12, 2020    (EP) .................................... 20201323
Feb. 26, 2021    (EP) .................................... 21159603

(51) Int. Cl.
    *A61K 39/215*       (2006.01)
    *A61P 31/14*        (2006.01)
    *A61K 39/00*        (2006.01)

(52) U.S. Cl.
    CPC ............ *A61K 39/215* (2013.01); *A61P 31/14* (2018.01); *A61K 2039/5154* (2013.01); *A61K 2039/5158* (2013.01); *A61K 2039/54* (2013.01); *A61K 2039/545* (2013.01)

(58) Field of Classification Search
None
See application file for complete search history.

(56) References Cited

FOREIGN PATENT DOCUMENTS

| CN | 111450244 A | 7/2020 |
| CN | 111548396 A | 8/2020 |
| CN | 111729079 A | 10/2020 |
| EP | 1448229 A2 | 8/2004 |
| EP | 2 360 173 A1 | 8/2011 |

OTHER PUBLICATIONS

Gowans et al., A phase I clinical trial of dendritic cell immunotherapy in HCV-infected individuals, 2010, Journal of Hepatology, vol. 53, pp. 599-607.*
European Search Report dated Mar. 26, 2021, issued by the European Patent Office in application No. EP 20 20 1323.
European Search Report dated Aug. 19, 2021, issued by the European Patent Office in application No. EP 21 15 9603.
Ali Golchin, "Cell-Based Therapy for Severe COVID-19 Patients: Clinical Trials and Cost-Utility", Stem Cell Reviews and Reports (2021)17:56-62, Spring Science+Business Media, LLC, part of Spring Nature 2020 (7 pages).
Anonymous Phase I-II Trial of Dendritic Cell Vaccine to Prevent COVID-19 in Adults—Full Text View—ClinicalTrials.gov., U.S. National Library of Medicine, pp. 1-6 (6 pages).
European Search Report for EP 20201323.1 dated Apr. 8, 2021.
Smita Nair, et al., "Isolation and Generation of Human Dendritic Cells", HHS Public Access, Curr Protoc Immunol. Author manuscript: available in PMC Sep. 3, 2015, pp. 1-31.

\* cited by examiner

*Primary Examiner* — Benjamin P Blumel
(74) *Attorney, Agent, or Firm* — Sughrue Mion, PLLC

(57) ABSTRACT

A pharmaceutical product for use as a vaccine against a viral disease in a human or animal subject, comprising three compositions comprising activated, autologous dendritic cells, loaded with three different SARS-CoV2 peptides, to be administered in three separate doses sequentially to the human or animal subject.

29 Claims, 19 Drawing Sheets

Specification includes a Sequence Listing.

D38

| D38 | PEPTIDE 1 | PEPTIDE 2 | PEPTIDE 3 |
|---|---|---|---|
| MEAN ± SEM | 132 ± 13 | 117 ± 11 | 120 ± 10 |
| P-VALUE | 0.01 | 0.1 | 0.05 |
| SAMPLES | 45 | 45 | 45 |

| IL-2 | PEPTIDE 1 | PEPTIDE 2 | PEPTIDE 3 |
|---|---|---|---|
| MEAN ± SEM | 126 ± 13 | 119 ± 8 | 152 ± 12 |
| P-VALUE | 0.06 | 0.02 | 0.0005 |
| SAMPLES | 19 | 19 | 19 |

FIG. 14a

| IFN-G | PEPTIDE 1 | PEPTIDE 2 | PEPTIDE 3 |
|---|---|---|---|
| MEAN ± SEM | 103 ± 5 | 121 ± 8 | 140 ± 14 |
| P-VALUE | NS | 0.01 | 0.009 |
| SAMPLES | 19 | 19 | 19 |

FIG. 14b

| TNF-A | PEPTIDE 1 | PEPTIDE 2 | PEPTIDE 3 |
|---|---|---|---|
| MEAN ± SEM | 117 ± 8 | 151 ± 20 | 146 ± 15 |
| P-VALUE | 0.04 | 0.02 | 0.006 |
| SAMPLES | 17 | 17 | 17 |

| IL-2 | PEPTIDE 1 | PEPTIDE 2 | PEPTIDE 3 |
|---|---|---|---|
| MEAN ± SEM | 133 ± 11 | 158 ± 16 | 168 ± 20 |
| P-VALUE | 0.01 | 0.004 | 0.007 |
| SAMPLES | 12 | 12 | 12 |

FIG. 15a

| IFN-G | PEPTIDE 1 | PEPTIDE 2 | PEPTIDE 3 |
|---|---|---|---|
| MEAN ± SEM | 104 ± 8 | 106 ± 12 | 132 ± 15 |
| P-VALUE | NS | NS | 0.05 |
| SAMPLES | 12 | 12 | 12 |

FIG. 15b

| TNF-A | PEPTIDE 1 | PEPTIDE 2 | PEPTIDE 3 |
|---|---|---|---|
| MEAN ± SEM | 121 ± 13 | 157 ± 21 | 163 ± 19 |
| P-VALUE | NS | 0.02 | 0.008 |
| SAMPLES | 11 | 11 | 11 |

| IL-2 | PEPTIDE 1 | PEPTIDE 2 | PEPTIDE 3 |
|---|---|---|---|
| MEAN ± SEM | 106 ± 8,4 | 101 ± 5 | 116 ± 9 |
| P-VALUE | NS | NS | NS |
| SAMPLES | 18 | 18 | 18 |

FIG. 16a

| IFN-G | PEPTIDE 1 | PEPTIDE 2 | PEPTIDE 3 |
|---|---|---|---|
| MEAN ± SEM | 95,5 ± 8 | 97,3 ± 8 | 111 ± 8 |
| P-VALUE | NS | NS | NS |
| SAMPLES | 18 | 18 | 18 |

FIG. 16b

| TNF-A | PEPTIDE 1 | PEPTIDE 2 | PEPTIDE 3 |
|---|---|---|---|
| MEAN ± SEM | 112 ± 9 | 115 ± 6 | 123 ± 14 |
| P-VALUE | NS | 0.03 | NS |
| SAMPLES | 16 | 16 | 16 |

| IL-2 | PEPTIDE 1 | PEPTIDE 2 | PEPTIDE 3 |
|---|---|---|---|
| MEAN ± SEM | 125 ±3,7 | 135 ± 8 | 154 ± 11 |
| P-VALUE | 0.000001 | 0,0009 | 0,0002 |
| SAMPLES | 14 | 14 | 14 |

FIG. 17a

| IFN-G | PEPTIDE 1 | PEPTIDE 2 | PEPTIDE 3 |
|---|---|---|---|
| MEAN ± SEM | 111 ± 10 | 116 ± 6 | 147 ± 12 |
| P-VALUE | NS | 0,03 | 0,002 |
| SAMPLES | 14 | 14 | 14 |

FIG. 17b

| TNF-A | PEPTIDE 1 | PEPTIDE 2 | PEPTIDE 3 |
|---|---|---|---|
| MEAN ± SEM | 123 ± 10 | 125 ± 16 | 140± 20 |
| P-VALUE | 0,04 | NS | NS |
| SAMPLES | 14 | 14 | 14 |

FIG. 17c

Non - infected

| IL-2 | PEPTIDE 1 | PEPTIDE 2 | PEPTIDE 3 |
|---|---|---|---|
| MEAN ± SEM | 90 ± 6 | 95 ± 7 | 95 ± 7 |
| P-VALUE | 0.01 | NS | NS |
| SAMPLES | 16 | 16 | 16 |

FIG. 18a

| IFN-G | PEPTIDE 1 | PEPTIDE 2 | PEPTIDE 3 |
|---|---|---|---|
| MEAN ± SEM | 107 ± 7 | 108 ± 8 | 121 ± 7 |
| P-VALUE | NS | NS | 0.009 |
| SAMPLES | 16 | 16 | 16 |

FIG. 18b

| TNF-A | PEPTIDE 1 | PEPTIDE 2 | PEPTIDE 3 |
|---|---|---|---|
| MEAN ± SEM | 86 ± 5 | 84 ± 4 | 95 ± 4 |
| P-VALUE | 0.01 | 0.0009 | NS |
| 16 | 16 | 16 | 16 |

FIG. 18c

|  | INFECTED | VACCINATED D180 | VACCINATED D38 | HEALTHY 1 | HEALTHY 2 |
|---|---|---|---|---|---|
| CD8+/PEPTIDE+ | 6,92 | 31,33 | 5,95 | 10,7 | 4,26 |
| MEMORY PLASMA/PEPTIDE+ | 1,84 | 10,68 | 3,02 | 1,7 | 0,47 |
| MEMORY T/ PEPTIDE + | 20,78 | 15,92 | 23,81 | 9,45 | 11,68 |

FIG. 19

SARS-COV-2 VACCINES

CROSS-REFERENCE TO RELATED APPLICATION

This application is a continuation of U.S. patent application Ser. No. 17/349,462, filed on Jun. 16, 2021, which claims priority from European Patent Application No. 20201323.1, filed on Oct. 12, 2020, and European Patent Application No. 21159603.6, filed on Feb. 26, 2021, in the European Patent Office, the disclosures of which are incorporated herein by reference in their respective entireties.

TECHNICAL FIELD

The present invention relates to the field of cellular immunology and immunotherapy. More specifically, the present invention relates to a method for inducing an immune response in a human or animal subject, as well as to a pharmaceutical composition and a kit of parts comprising such compositions for inducing an immune response. Furthermore, the present invention concerns a method for producing the pharmaceutical composition in vitro and the use of primed dendritic cells in a pharmaceutical composition or in a method for inducing an immune response. The present invention more specifically relates to a vaccine against the SARS Coronavirus 2 (SARS-CoV-2).

PRIOR ART

Pathogens, such as viruses, bacteria, fungi and parasites are organisms that can cause a disease, while some pathogens have be found to be responsible for severe effects and casualties in afflicted hosts.

Vaccination or administration of antibiotics can be useful in preventing or fighting disease arising from pathogens. The immune system of the human body provides defense against some common pathogens. Pathogens comprise proteins, so-called antigens that can be recognized by the immune system of the host. Antigens can belong to many different chemical classes and can derive from viral or bacterial proteins, lipids, carbohydrates, or combinations of these, such as lipoproteins or glycoproteins.

The adaptive immune system comprises two main mechanisms of immunity: Firstly, in humoral immunity, in which the immune system deals with freely circulating pathogenic antigens outside of infected cells, B-cells, by the aid of helper T cells and antigen presenting cells, differentiate into antibody-producing plasma B-cells against a specific antigen. These antibodies then bind to and neutralize the pathogenic antigens or cause lysis or phagocytosis. Secondly, in cellular immunity, which occurs inside infected cells, pathogenic antigens are expressed on the infected cell's surface or on an antigen presenting cell (APC). Helper T cells release cytokines that help activated CD8+ T cells bind to the infected cells' MHC-antigen complex and cause the CD8+ T cells to differentiate into cytotoxic T lymphocytes (CTL)—white blood cells that have the ability to kill other cells of the body in a highly specific manner. CTLs are CD8+ T cells that have been stimulated by peptides presented by the major histocompatibility complex class I (MHC I) on affected cells. After stimulation, they migrate through the tissues of the body to find and kill the target cells that are bearing the specific antigen. Antigen-specific CTLs proliferate to produce daughter cells with the same antigen specificity as the parent cells. The total number of those antigen-specific CTLs in the body is increased by the cell division of the activated CTLs. More importantly, some cells from both humoral (plasma cells) and cellular immunity (CTLs) will go on to differentiate into memory plasma cells or memory T cells. These are long lived cells that patrol the body and are on the look out for any subsequent invasion by the same pathogen. Memory cells are the basis of protective immunity or vaccination.

Dendritic cells (DCs) provide the signals that are required for the activation of T cells and they are potent APCs in the immune system. Interaction between the antigen presented by a MHC I or II protein or peptide that is present on the APCs and the T-cell receptor/CD3 complex is responsible for the specificity of the immune response. This interaction is necessary for T cell activation, but not sufficient. Interaction between receptor-ligand pairs of APCs and T cells generates costimulatory signals that can lead to induction of effector T cell functions and to the full proliferation of T cells.

T cells have the antigen-specific receptor, TCR, that recognizes a physical complex between host MHC proteins and small peptide fragments derived from protein antigens. The interaction between the peptide and MHC molecule is highly specific. MHC I molecules present peptide antigens to CD8+ T cells and MHCII molecules present peptides in CD4+ helper T cells. The size of those peptides that can be bound is 8 to 10 amino acids.

Immune recognition of pathogen-associated antigens is performed by specific CD8+ cytotoxic T lymphocytes that interact with the peptides that are bound to MHC I molecules. The in vitro stimulation of that interaction can be performed with the presentation of those molecules by APCs and especially the DCs. "Priming" or "pulsing" is the in vitro step, in which dendritic cells first contact the antigen and are then "primed or "loaded" with the respective antigen, i.e. present the antigenic peptide on their MHC I molecules. This is an essential step in the subsequent antigen presentation to the CD4+ or CD8+ T cells, i.e. T cell activation. CD8+ T cells that have been activated by the APCs (said activated CD8+ T cells are termed CTLs in the scope of this application) can recognize the same MHC/peptide complex on the target cells, i.e. pathogen-infected cells, and be triggered to kill them.

Immunotherapy therefore activates the subject's own immune system to recognize and kill the cells presenting antigens. The development of a successful strategy for treating a human disease requires an understanding of the responses of the immune cells that participate in the control of the pathogenic condition. The immune cells can be nonspecific effector cells, such as natural killer cells and macrophages, effector cells with limited diversity for antigen recognition, like $\gamma\delta$ T cells, and highly specific effector cells that have enormous diversity in antigen recognition such as antibody-producing B cells and $\alpha\beta$ T cells.

Epitope identification often involves derivation and testing of overlapping peptide libraries from the pathogen proteins that are based on known protein databases. Development and refinement of algorithms that predict pathogen-associated epitopes as well as the definition of preferred peptide-binding characteristics for MHC proteins that are associated with susceptibility to autoimmune disease or infection has been an important tool for the selection of epitopes with high immunogenicity.

The challenge has been the administration of an antigen to induce an immune response and keep it over time. In vitro, e.g. MHC I molecules can be loaded externally (ex vivo, in vitro) with a synthetic peptide to elicit CTL response, such as disclosed e.g. in EP1448229A2. In the same manner, MHCII molecules can also be loaded externally with a synthetic peptide to elicit B cell differentiation into plasma cells and antibody generation.

Due to the current Covid-19 pandemic, it has become an urgent need to find a vaccine against the SARS-CoV-2 virus. The present invention provides a vaccine comprising three doses with each one peptide of SARS-CoV-2 presented on dendritic cells, administered sequentially at three different points in time.

SUMMARY OF THE INVENTION

The present invention concerns a vaccine against SARS-CoV-2, by stimulating immune cells to recognize specific peptides of SARS-CoV-2, which eventually results in memory cell formation, i.e. formation of both memory plasma cell and central/effector memory T cell. The vaccine contains three populations of activated autologous dendritic cells (DCs) generated from mononuclear cells. For activation, each population of DCs is "pulsed" in vitro with a different SARS-CoV-2 peptide. Thus, this DC-based vaccine is administered in three doses, wherein dose 1 contains activated autologous DCs which have been activated with a first SARS-CoV-2 peptide, and is administered in week 1. Dose 2 contains activated autologous DCs which have been activated with a second SARS-CoV-2 peptide, the second peptide having been selected from a group of four different peptides, and is administered in week 2. Dose 3 contains activated autologous DCs which have been activated with a third SARS-CoV-2 peptide, and is administered in week 3.

The present invention concerns a pharmaceutical product comprising a first composition, a second composition and a third composition, wherein each of the first, second, and third compositions comprise one of three different populations of activated autologous DCs from a single human or animal subject. The activated autologous DCs in each of the three populations present a different peptide of a spike protein or of an envelope protein of SARS-CoV-2.

According to a first preferred embodiment, the first composition comprises a first population of activated autologous DCs which have been activated with a first peptide of a spike protein of SARS-CoV-2 or of an envelope protein of SARS-CoV-2, preferably of a spike protein of SARS-CoV-2. The second composition of the respective pharmaceutical product comprises a second population of activated autologous DCs which have been activated with a second peptide of a spike protein of SARS-CoV-2 or of an envelope protein of SARS-CoV-2, wherein the second peptide is different from the first peptide. The third composition of the respective pharmaceutical product comprises a third population of activated autologous DCs which have been activated with a third peptide of a spike protein of SARS-CoV-2 or of an envelope protein of SARS-CoV-2, preferably of a spike protein of SARS-CoV-2, wherein the third peptide is different from the first peptide and the second peptide.

The present invention further concerns the above mentioned pharmaceutical product for use as a vaccine, preferably for use as a vaccine against a viral disease caused by SARS-CoV-2 in a human or animal subject.

The present invention further concerns the above mentioned pharmaceutical product for use in treatment of a viral disease caused by SARS-CoV-2, preferably for use in treatment of COVID-19, wherein the three compositions described above are administered to the human or animal subject separately from each other and sequentially at three different points in time. Preferably, the first composition is administered to the human or animal subject in week 1, preferably on day 1, of a vaccination schedule, preferably by injection, wherein the second composition is administered to the human or animal subject in week 2, preferably on day 8, of the vaccination schedule, preferably by injection, and wherein the third composition is administered to the human or animal subject in week 3, preferably on day 15, of the vaccination schedule, preferably by injection. Advantageously, each composition is administered to the human or animal subject partially by intravenous and partially by subcutaneous injection. This is to be understood in that a part of the respective dose to be administered, comprising the respective composition to be injected is injected first intravenously, and the rest of the respective dose comprising the respective composition is injected subcutaneously.

The present invention furthermore concerns a kit of parts for use as a vaccine in a human or animal subject, comprising the pharmaceutical product as described above.

Said kit of parts is intended especially for use as a vaccine against a viral disease caused by SARS-CoV-2, more preferably for use as a vaccine against COVID-19. Said kit of parts comprises a first composition, a second composition and a third composition, wherein each of the first, second, and third compositions comprise one of three different populations of activated autologous DCs from a single human or animal subject, wherein the activated autologous DCs in each of the three populations present, preferably on one or more cell surface molecules, preferably on an MHC-complex, a different peptide of a spike protein of SARS-CoV-2 or an envelope protein of SARS-CoV-2.

The kit of parts according to a further preferred embodiment of the present invention comprises a first composition, a second composition and a third composition, wherein

- the first composition comprises a first population of activated autologous DCs of the human or animal subject which present on their cell surface a first peptide of a spike protein of SARS-CoV-2;
- the second composition comprises a second population of activated autologous DCs of the human or animal subject which present on their cell surface a second peptide of a spike protein of SARS-CoV-2 different from the first peptide, or of an envelope protein of SARS-CoV-2;
- the third composition comprises a third population of activated autologous DCs of the human or animal subject, which present on their cell surface a third peptide of a spike protein of SARS-CoV-2 different from the first peptide and the second peptide.

Preferably, the first composition comprises a first population of activated autologous DCs of the human or animal subject, which present on their cell surface a SARS-CoV-2 spike protein (84-92) LPFNDGVYF peptide (SEQ ID NO: 1).

The second composition preferably comprises a second population of activated autologous DCs of the human or animal subject which present on their cell surface one peptide selected from the group consisting of SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), and SARS-CoV-2 envelope protein (2-10) YSFVSEETG peptide (SEQ ID NO: 5).

The third composition preferably comprises a third population of activated autologous DCs of the human or animal subject, which present on their cell surface a SARS-CoV-2 spike protein (1185-1200) RLNEVAKNLNESLIDL peptide (SEQ ID NO: 6).

The administration sequence of the doses/compositions can also be altered.

The three compositions of a kit of parts according to a further preferred embodiment of the present invention are administered to the human or animal subject separately from each other and sequentially at three different points in time. Preferably, the three compositions are administered to the human or animal subject by injection, more preferably by a combination of intravenous and subcutaneous injections. Preferably 50-90% of each dose/composition are injected intravenously and the remaining 10-50% of each respective dose/composition are injected subcutaneously.

Preferably, the first composition is administered to the human or animal subject in week 1, preferably on day 1, of a vaccination schedule, wherein the second composition is administered to the same human or animal subject in week 2, preferably on day 8, of the vaccination schedule, and wherein the third composition is administered to the same human or animal subject in week 3, preferably on day 15 of the vaccination schedule.

The present invention further concerns a method of treating or preventing a viral disease caused by SARS-CoV-2 in a human or animal subject, comprising the followings steps:

administration of a first composition comprising a first population of activated autologous DCs of the human or animal subject which present on their cell surface a first peptide of a protein of SARS-CoV-2;

administration of a second composition comprising a second population of activated autologous DCs of the human or animal subject which present on their cell surface a second peptide of a protein of SARS-CoV-2;

administration of a third composition comprising a third population of activated autologous DCs of the human or animal subject which present on their cell surface a third peptide of a protein of SARS-CoV-2;

wherein each of the first, second, and third compositions comprise one of three different populations of activated autologous DCs of the human or animal subject, wherein in each of the three populations of activated autologous DCs, the activated autologous DCs present on their cell surface a different peptide of a spike protein or an envelope protein of SARS-CoV-2.

In a preferred method of treating a viral disease caused by SARS-CoV-2 in a human or animal subject, the first composition comprises a first population of activated autologous DCs of the human or animal subject which present on their cell surface a first peptide of a spike protein of SARS-CoV-2, wherein preferably the first composition comprises a first population of activated autologous DCs which present on their cell surface a SARS-CoV-2 spike protein (84-92) LPFNDGVYF peptide (SEQ ID NO: 1);

the second composition comprises a second population of activated autologous DCs of the human or animal subject which present on their cell surface a second peptide of a spike protein of SARS-CoV-2 different from the first peptide, or of an envelope protein of SARS-CoV-2, wherein preferably the second composition comprises a second population of activated autologous DCs which present on their cell surface one peptide selected from the group consisting of SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), and SARS-CoV-2 envelope protein (2-10) YSFVSEETG peptide (SEQ ID NO: 5);

the third composition comprises a third population of activated autologous DCs of the human or animal subject which present on their cell surface a third peptide of a spike protein of SARS-CoV-2 different from the first peptide and the second peptide, wherein preferably the third composition comprises a third population of activated autologous DCs which present on their cell surface a SARS-CoV-2 spike protein (1185-1200) RLNEVAKNLNESLIDL peptide (SEQ ID NO: 6).

According to a further preferred method of treating a viral disease caused by SARS-CoV-2 in a human or animal subject, the first, second and third composition are administered to the human or animal subject, i.e. the same human or animal subject, separately from each other and sequentially at three different points in time. Preferably, the first composition is administered to the human or animal subject in week 1, preferably on day 1 of a vaccination schedule, the second composition is administered to the same human or animal subject in week 2, preferably on day 8 of the vaccination schedule, and the third composition is administered to the same human or animal subject in week 3, preferably on day 15 of the vaccination schedule.

The present invention furthermore concerns a method for obtaining a population of human or animal autologous dendritic cells (DCs) presenting a viral antigenic peptide, preferably a SARS-CoV-2 peptide. Preferably, the respective peptide is selected from the following group consisting of SARS-CoV-2 spike protein (84-92) LPFNDGVYF peptide (SEQ ID NO: 1), SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), SARS-CoV-2 envelope protein (2-10) YSFVSEETG peptide (SEQ ID NO: 5), and SARS-CoV-2 spike protein (1185-1200) RLNEVAKNLNESLIDL peptide (SEQ ID NO: 6), for the preparation of a pharmaceutical product or for the preparation of a kit of parts as described above, comprising the following steps:

a.) culturing monocytes isolated from PBMCs of the human or animal subject, said monocytes preferably isolated by density gradient centrifugation, such as e.g. Biocoll/Ficoll-separation, or by Red Blood Lysis with $NH_4Cl$ and magnetic bead isolation (monocyte enrichment kit);

b.) culturing of adhering monocytes of step a.) with GM-CSF and IL-4, preferably in RPMI 1640 Medium with 10% heat-inactivated FBS and 1% glutamine, preferably for 6 days, resulting in a population of immature DCs;

c.) pulsing of the immature DCs of step b.), preferably on day 6 of culture, with an antigenic peptide, preferably at a final concentration of 10 µg/ml, and incubation, preferably for 4-24 hours, in case of SARS-CoV-2 spike protein (84-92) LPFNDGVYF peptide (SEQ ID NO: 1) or SARS-CoV-2 spike protein (1185-1200) RLNEVAKNLNESLIDL peptide (SEQ ID NO: 6) preferably in the presence of β2 microglobulin, preferably at a final concentration of 3-10 µg/ml of β2 microglobulin, the incubation resulting in a population of loaded dendritic cells presenting the viral antigenic peptide; and preferably d.) cryo-preserving the loaded DCs until further use;

and optionally, after step c.) and preferably prior to step d.), e.) maturing of the loaded DCs of step c.) presenting the viral antigenic peptide to MHCI by incubation with a cytokine cocktail, preferably by incubation for 48 h at 37° C. and 5% $CO_2$.

In case the loaded DCs obtained in step c.) present the viral antigenic peptide on their MHC I, in optional step e.), the maturing step is carried out with a cytokine cocktail preferably including IL-6, preferably IL-6 at a concentration of 10 ng/ml, IL-1β, preferably IL-1β at a concentration of 25 ng/ml, TNF-α, preferably TNF-α at a concentration of 50 ng/ml, and PGE2, preferably PGE2 at a concentration of $10^{-6}$ M. In this case, the loaded DCs activate T cells in the subject's body, which are turned into CTL, which then kill infected cells.

In case the loaded DCs obtained in step c.) present the viral antigenic peptide on their MHC II, in optional step e.), the maturing step is carried out with a cytokine cocktail preferably including GM-CSF, IL-4, TNF-α, sCD40L, IL-6, IL-21, IL-10 and anti-human IgM. In this case, preferably the following concentration ranges are used: 1-200 ng/ml GM-CSF, 1-200 ng/ml IL-4, 1-200 ng/ml TNF-α, 1-100 µg/ml sCD40L, 1-200 ng/ml IL-6, 1-200 ng/ml IL-21, 1-200 ng/ml IL-10, 1-100 µg/ml anti-human IgM. In this case, the loaded DCs activate T helper cells which then activate B cells to turn into antibody-secreting plasma cells.

Preferably, the loaded DCs are contained in the pharmaceutical product according to the invention and injected in an immature form, i.e. after step c.) or after step d.) in case cryopreservation is desired or necessary. In this case, the maturation of the loaded DCs takes place inside the body of the vaccinated human or animal subject. Alternatively, the loaded DCs are contained in the pharmaceutical product according to the invention and injected in a mature form after going through a maturation process described in step e.) above.

In the production of a vaccine or kit of parts, comprising three compositions comprising loaded dendritic cells, the method described above for obtaining a population of human or animal autologous dendritic cells presenting an viral antigenic peptide, i.e. the method for obtaining a population of loaded dendritic cells, is conducted separately with each selected individual peptide in step b.), thereby yielding three separate compositions of autologous loaded dendritic cells, wherein in each of the three compositions, the loaded DCs present a different peptide.

The present invention therefore furthermore concerns a method for the production of a medicament, comprising the following steps:

a.) culturing monocytes isolated from PBMCs of a human or animal subject, said monocytes preferably isolated by density gradient centrifugation (e.g. Biocoll/Ficoll-separation) or by Red Blood Lysis with $NH_4Cl$ and magnetic bead isolation (monocyte enrichment kit);

b.) culturing of adhering monocytes of step a.) with GM-CSF and IL-4, preferably in RPMI 1640 Medium with 10% heat-inactivated FBS and 1% glutamine, preferably for 6 days, resulting in a population of immature dendritic cells;

c.) pulsing of the immature dendritic cells of step b.), preferably on day 6 of culture, with a first antigenic peptide, selected from the following group consisting of SARS-CoV-2 spike protein (84-92) LPFNDGVYF peptide (SEQ ID NO: 1), SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), SARS-CoV-2 envelope protein (2-10) YSFVSEETG peptide (SEQ ID NO: 5), and SARS-CoV-2 spike protein (1185-1200) RLNEVAKNLNESLIDL peptide (SEQ ID NO: 6), preferably at a final concentration of 10 µg/ml, and incubation, preferably for 4-24 hours, in case of SARS-CoV-2 spike protein (84-92) LPFNDGVYF peptide (SEQ ID NO: 1) or SARS-CoV-2 spike protein (1185-1200) RLNEVAKNLNESLIDL peptide (SEQ ID NO: 6) preferably in the presence of β2 microglobulin, preferably at a final concentration of 3 µg/ml of β2 microglobulin, the incubation resulting in a population of loaded dendritic cells presenting the viral antigenic peptide; and repeating steps a.) to c.) twice with in each case a different peptide, to produce the second and third population of loaded dendritic cells, wherein step b.) results in a first, second and third population of immature dendritic cells, respectively, and wherein in step c.), the first, second and third population of immature dendritic cells, respectively, is pulsed with a first, second and third antigenic peptide, respectively, wherein the second and third antigenic peptides, respectively, are each different from the first antigenic peptide, and wherein the second and the third antigenic peptides are different from each other, and wherein the first, the second and the third antigenic peptides are each selected from the following group consisting of SARS-CoV-2 spike protein (84-92) LPFNDGVYF peptide (SEQ ID NO: 1), SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), SARS-CoV-2 envelope protein (2-10) YSFVSEETG peptide (SEQ ID NO: 5), and SARS-CoV-2 spike protein (1185-1200) RLNEVAKNLNESLIDL peptide (SEQ ID NO: 6), preferably at a final concentration of 10 µg/ml.

Step c.) is followed in each case by an incubation, preferably for 4-24 hours, in case of SARS-CoV-2 spike protein (84-92) LPFNDGVYF peptide (SEQ ID NO: 1) or SARS-CoV-2 spike protein (1185-1200) RLNEVAKNLNESLIDL peptide (SEQ ID NO: 6);

Preferably, step c.) and, if necessary, the following incubation, is followed by d.) cryo-preserving the loaded dendritic cells acquired in step c.), until further use; and optionally, prior to step d.), e.) maturing of the loaded dendritic cells presenting the first, second or third viral antigenic peptide, respectively, of step c.) with a cytokine cocktail, preferably including IL-6, preferably IL-6 at a concentration of 10 ng/ml, IL-1β, preferably IL-1β at a concentration of 25 ng/ml, TNF-α, preferably TNF-α at a concentration of 50 ng/ml, and PGE2, preferably PGE2 at a concentration of 10-6 M, and incubation, preferably incubation for 48 h at 37° C. and 5% $CO_2$.

The terms "vaccine" or "vaccine treatment" in the context of this application is to be understood as a prophylactic treatment, in which an immune response, especially against a viral disease caused by SARS-CoV-2, is activated in the body of the human or animal subject after following a specific vaccination schedule. By the inventive vaccine comprising the pharmaceutical product according to the invention, the immune response is triggered to be produced. In case the subject already produced an immune response, but an insufficient response to eliminate the virus, this response can be increased by the inventive vaccine.

The term "week 1/2/3", respectively, is to be understood in that dose 1 of the vaccine, preferably comprising DCs loaded with a first peptide (Seq. ID 1), is administered on day 1 of a vaccination schedule. Approximately one week after dose 1, preferably on day 8 of the vaccination schedule, dose 2, comprising DCs loaded with a second peptide selected from a group of four peptides (Seq. ID 2-5), is administered to the same subject, and approximately one week after dose 2, preferably on day 15 of the vaccination schedule, dose 3, comprising DCs loaded with a third peptide (Seq. ID 6), is administered. However, the time between the days of administration may vary, depending on the status of the individual subject's immune system. The sequence of administration of the doses 1-3 can also be altered, such as for example dose 1-2-3, 1-3-2, 2-1-3, 2-3-1, 3-1-2, or 3-2-1.

The terms "primed/pulsed/loaded/activated dendritic cells" are to be understood as dendritic cells which present the respective peptide on a cell surface molecule, i.e. MHC I/II.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIGS. 1a-1b, 2a-2c, 3a-3b, 4, 5a-5b, 6a-6c, 7a-7b, 8a-8b, 9a-9c, 10a-10b, 11a-11b, 12a-12c, 13a-13b, 14a-14c, 15a-15c, 16a-16c, 17a-17c, 18a-18c, and 19 show the results of an analysis of a number of vaccinated individuals at 38, 76, 120, and 180 days after the administration of composition 1, i.e. dose 1, respectively: For flow cytometry, 35 individuals for 38 days, 32 individuals for 76 days and 8 individuals for 120 days after the administration of composition 1, i.e. dose 1. The results showed a determination of the percentage of plasma cells, memory plasma cells, effector T cells, central memory T cells, effector memory T cells, IgG positive cells and IgM positive cells using flow cytometry. For serum IgG determination, 45 individuals for 38 days, 31 individuals for 76 days, 19 individuals for 120 days, and 13 individuals for 180 days after the administration of composition 1, i.e. dose 1. SARS-COV-2 specific IgG in serum was detected specifically for the three peptides used in pulsing compared to uninfected individuals and/or sera at baseline. For cell-mediated immunity, 19 individuals for 38 days, 12 individuals for 76 days, 18 individuals for 120 days for IL-2 and IFN-γ and 16 individuals for 120 days for TNF-α and 14 individuals for 180 days after the administration of composition 1, i.e. dose 1. SARS-COV-2 specific cellular immunity was detected specifically for the three peptides used in pulsing by detection of secreted IL-2 and/or TNF-alpha and/or IFN-gamma. In the figures, FIG. 1a-1b shows in FIG. 1a the percentage of individuals with increased plasma cells and in FIG. 1b with increased memory plasma cells on day 38 (D38) compared to the baseline (humoral immunity);

FIG. 2a-2c shows in FIG. 2a the percentage of individuals with increased effector T cells, in FIG. 2b with increased effector memory T cells and in FIG. 2c with increased central memory T cells on day 38 compared to the baseline (cellular immunity);

FIG. 3a-3b shows in FIG. 3a the percentage of individuals with increased IgG positive cells and in FIG. 3b with increased IgM positive cells on day 38 compared to the baseline;

FIG. 4 shows a table indicating whether the increases in serum IgG levels against the three peptides used for DC pulsing on day 38 compared to the baseline are significant or not;

FIG. 5a-5b shows in FIG. 5a the percentage of individuals with increased plasma cells and in FIG. 5b with increased memory plasma cells on day 76 (D76) compared to day 38 (humoral immunity);

FIG. 6a-6c shows in FIG. 6a the percentage of individuals with increased effector T cells, in FIG. 6b with increased effector memory T cells and in FIG. 6c with increased central memory T cells on day 76 compared to day 38 (cellular immunity);

FIG. 7a-7b shows in FIG. 7a the percentage of individuals with increased IgG positive cells and in FIG. 7b with increased IgM positive cells on day 76 compared to day 38;

FIG. 8a-8b shows in FIG. 8a the percentage of individuals with increased plasma cells and in FIG. 5b with increased memory plasma cells on day 120 (D120) compared to day 76 (humoral immunity);

FIG. 9a-9c shows in FIG. 9a the percentage of individuals with increased effector T cells, in FIG. 9b with increased effector memory T cells and in FIG. 9c with increased central memory T cells on day 120 compared to day 76 (cellular immunity);

FIG. 10a-10b shows in FIG. 10a the percentage of individuals with increased IgG positive cells and in FIG. 10b with increased IgM positive cells on day 120 compared to day 76;

FIG. 11a-11b shows in FIG. 11a the percentage of individuals with increased plasma cells and in FIG. 11b with increased memory plasma cells on day 180 (D180) compared to day 120 (D120) (humoral immunity);

FIG. 12a-12c shows in FIG. 12a the percentage of individuals with increased effector T cells, in FIG. 12b with increased effector memory T cells and in FIG. 12c with increased central memory T cells on day 180 compared to day 120 (cellular immunity);

FIG. 13a-13b shows in FIG. 13a the percentage of individuals with increased IgG positive cells and in FIG. 13b with increased IgM positive cells on day 180 compared to day 120;

FIG. 14a-14c shows in FIG. 14a a table indicating the percentage of individuals with statistically increased cell mediated immunity against the three peptides used for DC pulsing on day 38 with respect to IL-2 secretion; and in FIG. 14b a table indicating the percentage of individuals with statistically increased cell mediated immunity against the three peptides used for DC pulsing on day 38 with respect to IFN-gamma secretion; and in FIG. 14c a table indicating the percentage of individuals with statistically increased cell mediated immunity against the three peptides used for DC pulsing on day 38 with respect to TNF-alpha secretion;

FIG. 15a-15c shows in FIG. 15a a table indicating the percentage of individuals with statistically increased cell mediated immunity against the three peptides used for DC pulsing on day 76 with respect to IL-2 secretion; and in FIG. 15b a table indicating the percentage of individuals with statistically increased cell mediated immunity against the three peptides used for DC pulsing on day 76 with respect to IFN-gamma secretion; and in FIG. 15c a table indicating the percentage of individuals with statistically increased cell mediated immunity against the three peptides used for DC pulsing on day 76 with respect to TNF-alpha secretion;

FIG. 16a-16c shows in FIG. 16a a table indicating the percentage of individuals with statistically increased cell mediated immunity against the three peptides used for DC pulsing on day 120 with respect to IL-2 secretion; and in FIG. 16b a table indicating the percentage of individuals with statistically increased cell mediated immunity against the three peptides used for DC pulsing on day 120 with respect to IFN-gamma secretion; and in FIG. 16c a table indicating the percentage of individuals with statistically increased cell mediated immunity against the three peptides used for DC pulsing on day 120 with respect to TNF-alpha secretion;

FIG. 17a-17c shows in FIG. 17a a table indicating the percentage of individuals with statistically increased cell mediated immunity against the three peptides used for DC pulsing on day 180 with respect to IL-2 secretion; and in FIG. 17b a table indicating the percentage of individuals with statistically increased cell mediated immunity against the three peptides used for DC pulsing on day 180 with respect to IFN-gamma secretion; and in FIG. 17c a table indicating the percentage of individuals with statistically increased cell mediated immunity against the three peptides used for DC pulsing on day 180 with respect to TNF-alpha secretion;

FIG. 18a-18c shows in FIG. 18a a table indicating the percentage of non-infected/non vaccinated individuals with statistically increased cell mediated immunity against the three peptides used for DC pulsing with respect to IL-2 secretion; and in FIG. 18b the percentage of non-infected/non vaccinated individuals with statistically increased cell mediated immunity against the three peptides used for DC pulsing with respect to IFN-gamma secretion; and in FIG. 18c the percentage of non-infected/non-vaccinated individuals with statistically increased cell mediated immunity against the three peptides used for DC pulsing with respect to TNF-alpha secretion;

FIG. 19. shows in FIG. 19 a table indicating the specificity of immunity against SARS-COV-2 peptides used for pulsing; CD8 positive cells specific for the three peptides used, memory plasma cells specific for the three peptides used and memory T cells specific for the three peptides used were determined in one infected individual, two individuals that have received the vaccine according to the invention, determined on day 38 and 180, respectively, and two non-infected individuals.

DESCRIPTION OF PREFERRED EMBODIMENTS

Figure 1A:
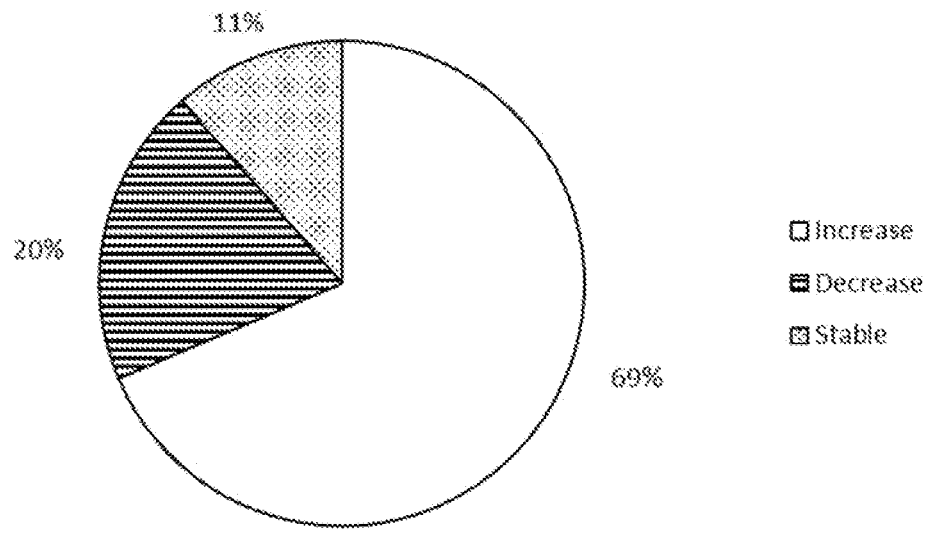
Figure 1B:
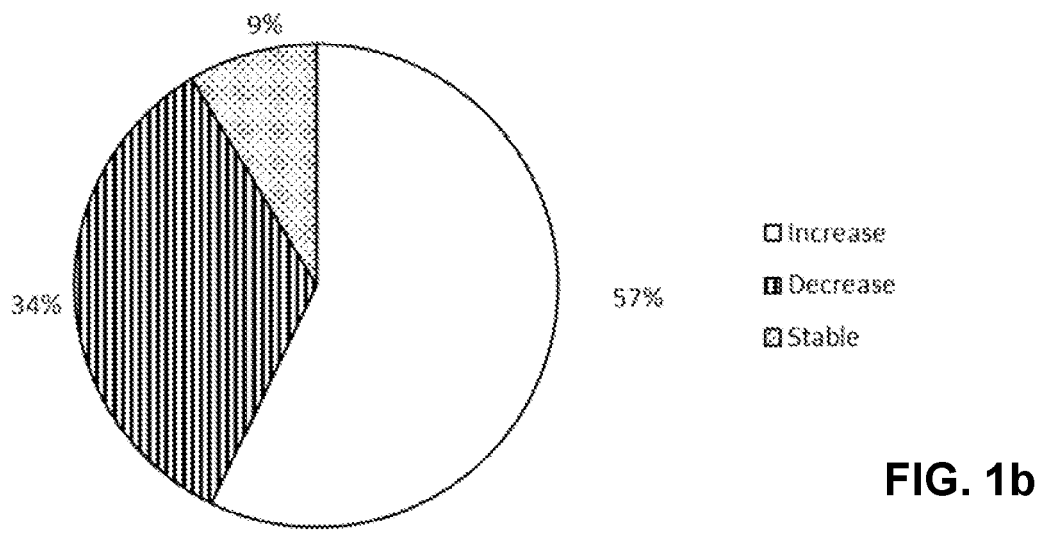
Figure 2A:
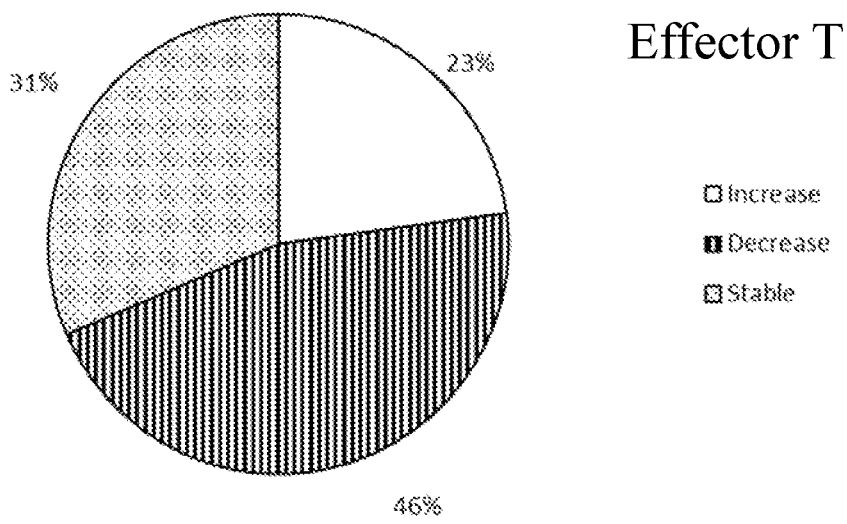
Figure 2B:
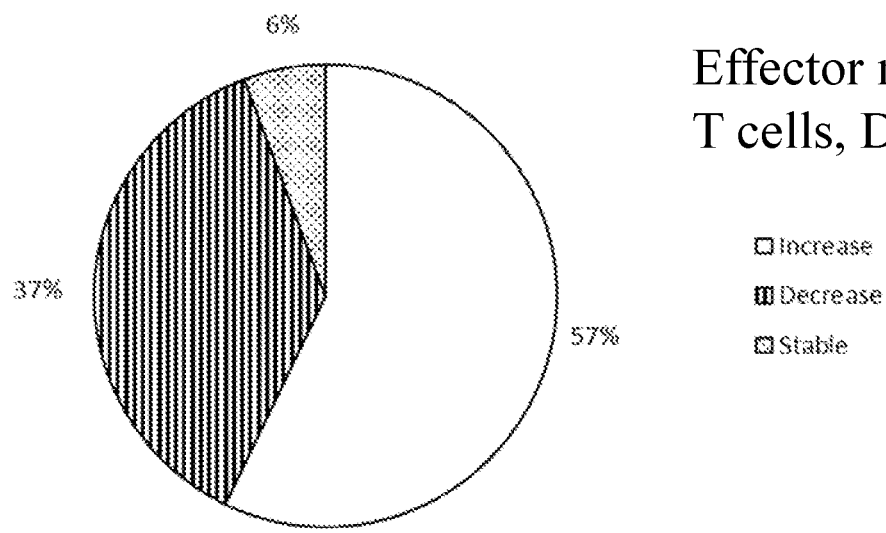
Figure 2C:
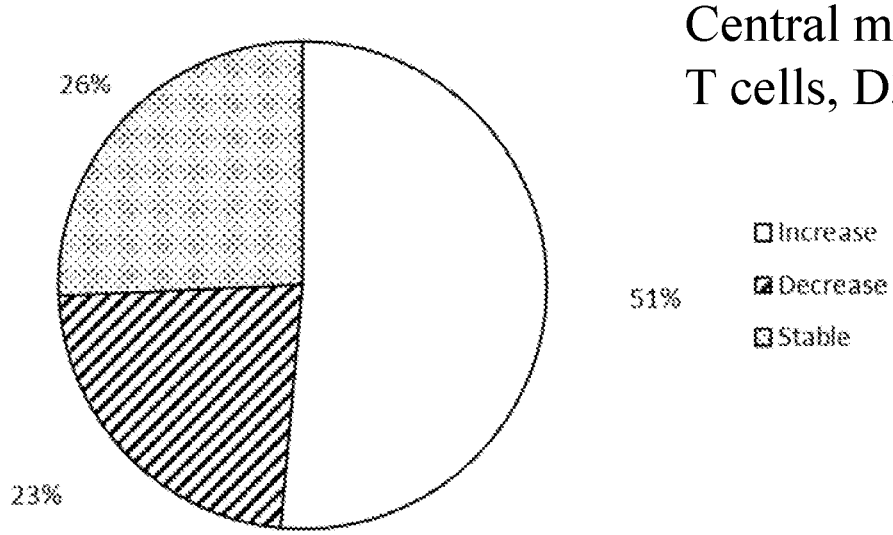
Figure 3A:
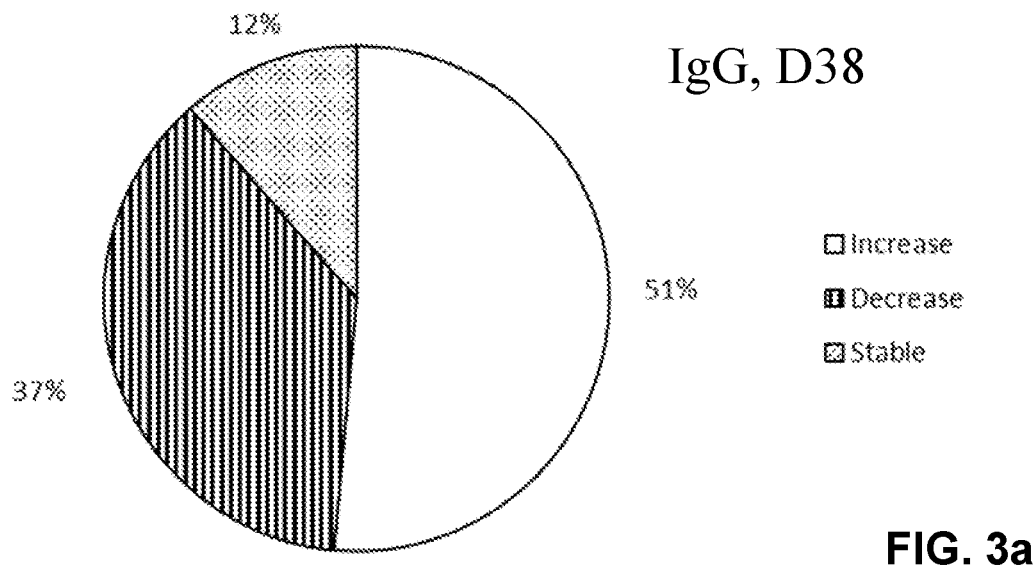
Figure 3B:
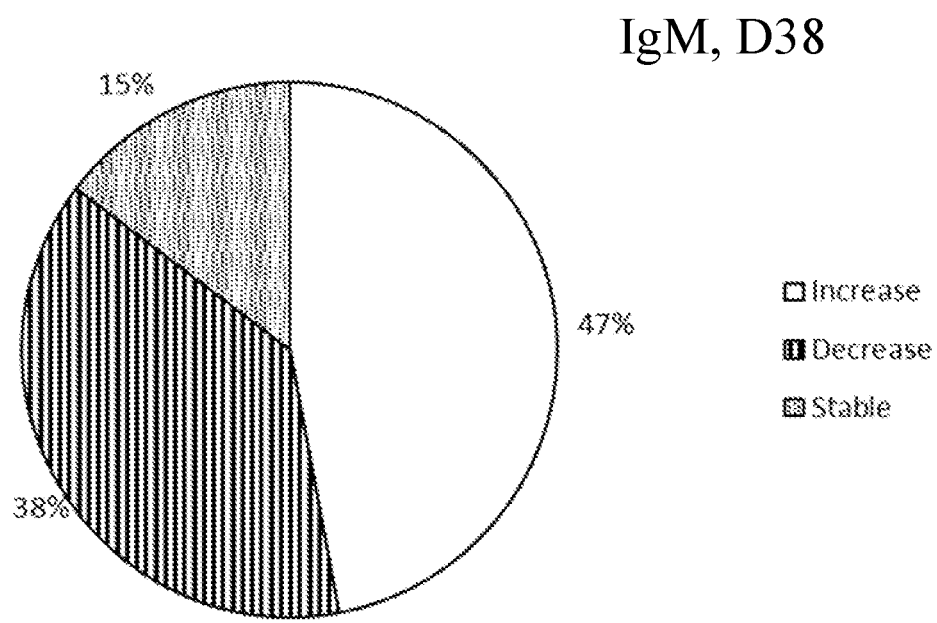

The peptides were selected according to their ability to activate the immune system. For the peptide sequence design, a number of publically available T-cell epitope prediction tools were used. These tools were selected according to Sanchez-Trincado et al, 2017 (J. L. Sanchez-Trincado, M. Gomez-Perosanz, P. A. Reche, "Fundamentals and Methods for T- and B-Cell Epitope Prediction", *Journal of Immunology Research*, vol. 2017, Article ID 2680160).

Dose 1 of the vaccine, comprising a first composition comprising SARS-CoV-2 spike protein (84-92) LPFNDGVYF peptide (SEQ ID NO: 1), to be administered in week 1, and dose 3 of the vaccine, comprising a third composition comprising SARS-CoV-2 spike protein (1185-1200) RLNEVAKNLNESLIDL peptide (SEQ ID NO: 6), to be administered in week 3, were designed to activate cellular, i.e. CTL-mediated immunity. Dose 2 of the vaccine, comprising a second composition comprising one peptide selected from the group consisting of SARS-CoV-2 spike protein (326-340) IVRFPNITNLCPFGE peptide (SEQ ID NO: 2), SARS-CoV-2 spike protein (718-726) FTISVTTEI peptide (SEQ ID NO: 3), SARS-CoV-2 spike protein (449-463) YNYLYRLFRKSNLKP (SEQ ID NO: 4), and SARS-CoV-2 envelope protein (2-10) YSFVSEETG peptide (SEQ ID NO: 5), was designed to activate humoral, i.e. antibody-mediated immunity. All four peptides for dose 2 were found to be immunogenic for the activation of immunity via MHC II by the algorithm used for immunogenicity determination.

Dendritic Cell Generation

Example 1

The initial sample consisted of 50 ml of peripheral blood of a human subject. 40 ml of whole blood were lysed with $NH_4Cl$. Cells were then washed with PBS. Supernatant was discarded and cell pellet was re-suspended in 100 µl Monocyte Enrichment Cocktail from Monocyte Enrichment Set (558454, BD), containing magnetic beads conjugated with an antibody specific for the selection of monocytes. Cells were incubated for 15 minutes. After the incubation period, the cell pellet was resuspended in 5 ml PBS and washed by centrifugation for 5 minutes, 200×g, wherein ×g" stands for times gravity (unit of relative centrifugal force (RCF)). The supernatant was discarded and the cell pellet was incubated with 100 µl of Streptavidin Particles Plus from the same Monocyte Enrichment Set. The cell pellet was then incubated for 30 minutes. After the incubation period, 1 ml of PBS was added and the tube was positioned in a magnetic separation rack for eppendorf tubes for 10 minutes. After incubation, the supernatant, i.e. the negative fraction containing mononuclear cells, was collected, added in 10 ml PBS and washed by centrifugation for 5 minutes at 200×g. The supernatant was discarded and the cell pellet was resuspended in 15 ml RPMI supplemented with 10% FBS, 200 mM L-glutamine, GM-CSF and IL-4, preferably 1-200 ng/ml of GM-CSF and 1-200 ng/ml of IL-4. The 15 ml of medium containing the cells were divided into three T-25 culture flasks (one for production of each dose/activation with one of the separate peptides) for 6 days at 37° C., at 5% $CO_2$. Half way through the culture period, medium was replenished.

Example 2

Alternatively to the dendritic cell generation of example 1, peripheral blood mononuclear cells (PBMCs) were isolated from freshly collected blood samples in vacutainers containing EDTA. PBMCs were isolated using density gradient centrifugation (e.g. Biocoll or Ficoll separation). The cell pellet was resuspended in RPMI supplemented with 10% FBS and 200 mM L-glutamine and left for 2 hours until monocyte adherence. The rest of the cells was discarded and adhered cells were cultured in the presence of 10 ml fresh RPMI (e.g. RPMI 1640) supplemented with 10% FBS, 200 mM L-glutamine, GM-CSF and IL-4, preferably 1-200 ng/ml of GM-CSF, and preferably 1-200 ng/ml of IL-4.

As in example 1, the 15 ml of medium containing the cells were divided into three T-25 culture flasks (one for production of each dose/activation with one of the separate peptides) for 6 days at 37° C., at 5% $CO_2$. Half way through the culture period, medium was replenished.

Pulsing of the DCs

After 6 days, the DCs were isolated and cultured according to one of the methods described in examples 1 or 2 above, and then pulsed with the addition of 10 µg/ml of one of the following peptides for 4 to 24 hours.

Figure 5A:
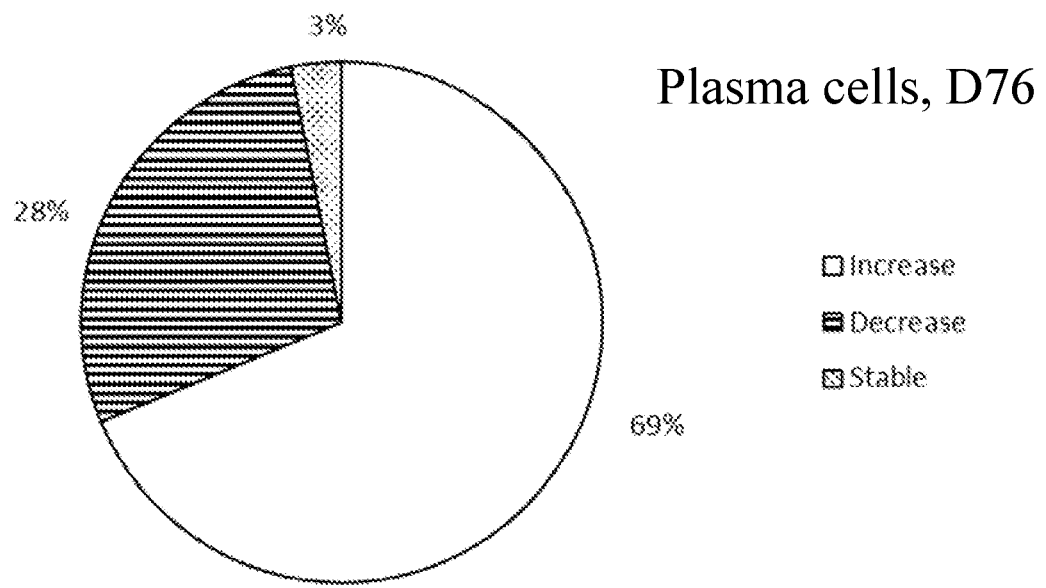
Figure 5B:
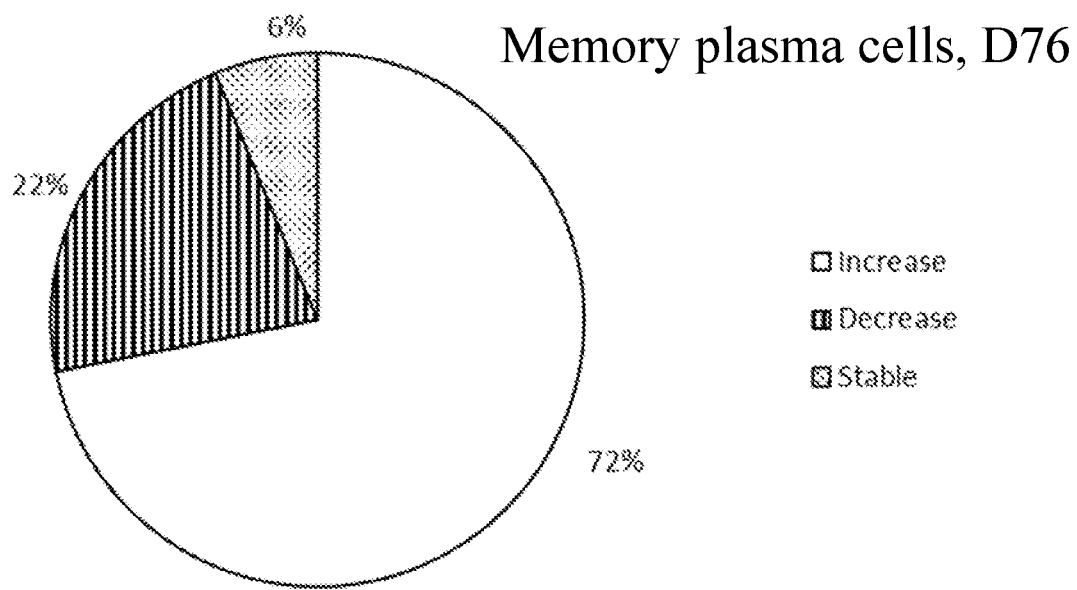

```
Peptide 1: SARS-CoV-2 spike protein (84-92)
                                    (SEQ ID NO: 1)
LPFNDGVYF peptide;

Peptide 2: SARS-CoV-2 spike protein (326-340)
                                    (SEQ ID NO: 2)
IVRFPNITNLCPFGE peptide Peptide 3: SARS-CoV-2 spike protein (718-726)
                                    (SEQ ID NO: 3)
FTISVTTEI peptide Peptide 4: SARS-CoV-2 spike protein (449-463)
                                    (SEQ ID NO: 4)
YNYLYRLFRKSNLKP, Peptide 5: SARS-CoV-2 envelope protein (2-10)
                                    (SEQ ID NO: 5)
YSFVSEETG peptide;

Peptide 6: SARS-CoV-2 spike protein (1185-1200)
                                    (SEQ ID NO: 6)
RLNEVAKNLNESLIDL peptide
```

Peptide 1 is to be used for pulsing DCs in the preparation of dose 1 of the vaccine. Peptide 2 was selected for pulsing DCs in the preparation of dose 2 of the vaccine, and peptide 6 was used for pulsing DCs in the preparation of dose 3 of the vaccine.

In the case of peptides 1 and 6, in each case 1-10 μg/ml b2 microglobulin were added to the DCs for the pulsing step. This is due to the fact that peptides 1 and 6, respectively, are presented by the MHC I complex on the cell surface of DCs, which results in an activation of T cells (cellular immunity). Peptides 2, 3, 4 and 5 are presented by the MHC II complex of DCs, which results in an activation of B cells (humoral immunity). Microglobulin was only added for the peptides presented by the MHC I complex.

The pulsed DCs were still immature, i.e. the maturation occurs in vivo after injection.

After pulsing, DCs from each flask were collected and cryo-preserved until further use.

Injection of Doses 1/2/3 of Vaccine

For use, i.e. for injection, DCs of the selected first, second or third dose were thawed and washed with PBS. The cell pellet was resuspended in 6 ml of 0.45% NaCl prior to injection. Thus, each dose had a volume of 6 ml. Of this volume, in each case, for each dose, 1 ml of the respective composition was injected in the human subject (individuals 1-10) subcutaneously, and the remaining 5 ml of the injection volume of the composition were subsequently injected to the same respective subject intravenously.

All three doses of the vaccine, each comprising one composition comprising a population of activated autologous DCs, were injected into the same human subject with in each case approximately 1 week in between the doses of administration. In total, feedback data is available of 16 vaccinated individuals for Day 76 and of 13 vaccinated individuals for day 38.

Follow-Ups

Follow up blood samples were collected from each of the 10 individual human subjects on day 38 and day 76 after the first injection to assess immunity. Preferably, follow up blood samples are to be collected at days 38, 76, 180, 364 (approx. after 1 month, 2-3 months, 6 months, and 12 months) after the first injection to assess immunity. Analysis of the blood samples collected at the specified points in time provides information about immune status after the vaccination. Performed tests include the following:

5 ml of whole blood were treated with $NH_4Cl$ for RBC lysis. The cell pellet was washed with 10 ml PBS for 5 minutes at 200×g. The cell pellet was resuspended in 1.5 ml PBS and 100 μl of the suspension were added in each one of 11 flow cytometry tubes. The cells were stained with the following antibodies: CD19, CD138, CD27, IgG, IgM, CD62L, CD197, CD45RO. From the analysis of the above tubes, the percentage of immature B cells, plasma cells, memory plasma cells, naïve T cells, effector T cells, central memory T cells, effector memory T cells, IgG positive cells and IgM positive cells can be determined.

5 ml of whole blood were centrifuged for serum separation. The serum was collected and stored at −20° C. The serum was used in a commercial lateral flow assay to test the presence of SARS-CoV-2 IgG and IgM levels.

From the isolated serum, furthermore the presence of IgG and IgM specific for the peptides used in DC pulsing, was determined. This was achieved using peptide-based ELISA using 100 μl/well of peptide at 2 μg/ml. After 24 hours of incubation, wells were washed five times with PBS and incubated with 100 μl of serum either from an uninfected individual (probe 11) or from individuals that have received the vaccine (probes 1-10). After 24 hours, wells were washed five times with PBS and incubated with anti-human IgG antibody, conjugated with HRP. After 1 hour of incubation, wells were washed five times with PBS and 100 μl of TMB were added for 10 minutes or until color development. The reaction was stopped by the addition of 100 μl of stop buffer. Absorbance was determined at 450 nm using a uQuant microplate spectrophotometer.

T cell (CD3), T-helper cell (TH-cell, i.e. CD4), B cell (CD19) and NK cell counts were determined before and after administering each dose of the vaccine.

Analysis of Follow-Ups:

In FIG. 1*a*, on day 38, the increase (>25%) in plasma cells shown in 69% of the individuals on day 38 indicates antibody generation. In FIG. 1*b*, the increase (>25%) in memory plasma cells in 57% of the individuals indicates protective memory cell formation of the humoral immunity.

In FIG. 2*a*, on day 38, 23% of the individuals showed an increase (>25%) in effector T cells, in FIG. 2*b*, 57% showed an increase (>25%) in effector memory cells and in FIG. 2*c*, 51% showed and increase (>25%) in central memory cells. The increase shown on day 38 in both effector and central memory T cell generation indicates protective memory cell formation of the cellular immunity.

In FIG. 3*a*, on day 38, 51% of individuals showed an increase (>25%) in IgG positive cells and in FIG. 3*b*, 47% of the individuals showed an increase in IgM positive cells. The increase in both IgG and IgM positive cells shown for day 38 in about half of the individuals indicates an increased generation of IgG and IgM antibodies, and thus the activation of humoral immunity.

The table shown in FIG. 4, indicates that on day 38, there was a statistical increase in serum IgG specific for SARS-COV-2 for peptides 1 and 3. The level of statistical significance is often expressed as a p-value between 0 and 1. A p-value less than 0.05 (typically 0.05) is statistically significant. It indicates strong evidence against the null hypothesis, as there is less than a 5% probability the null is correct (and the results are random). The results shown in FIG. 4 indicate that the activation of immunity was specific for the peptides used. On days 76, 120 and 180, the increases in serum IgG against any of the three peptides were not significant (results not shown).

As indicated in FIG. 5a, on day 76, 69% of individuals showed an increase (>25%) of plasma cells and, as shown in FIG. 5b, 72% showed an increase (>25%) in memory plasma cells. The further increase in plasma cells and memory plasma cells on day 76 in more than ⅔ of the individuals indicates that more individuals developed protective memory cell formation of the humoral immunity.

Figure 6A:
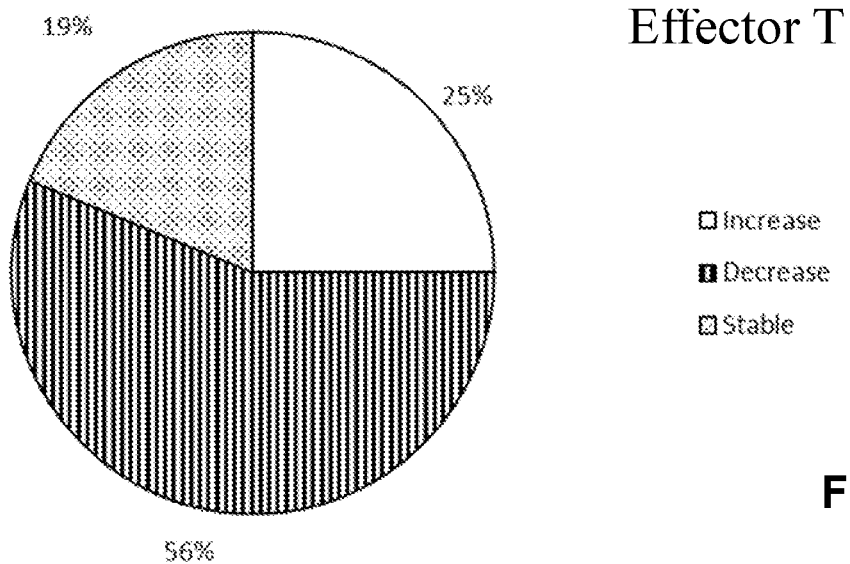
Figure 6B:
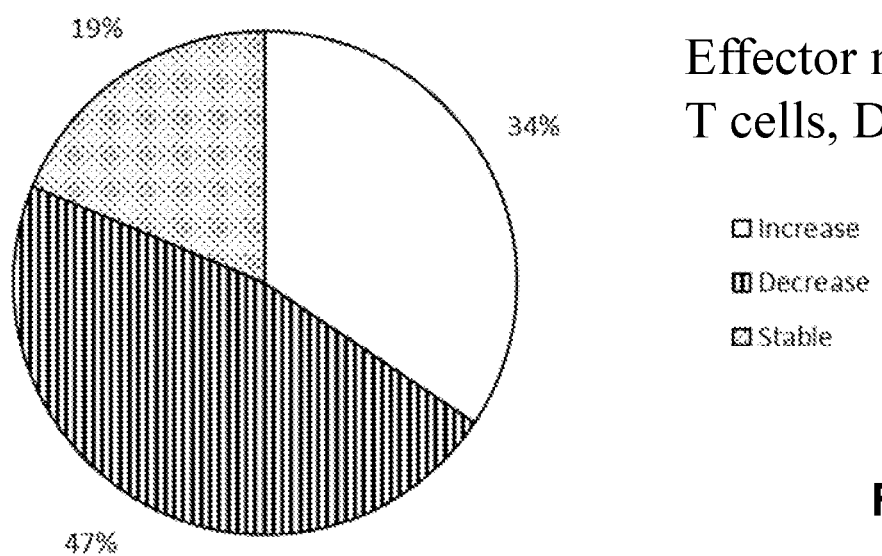
Figure 6C:
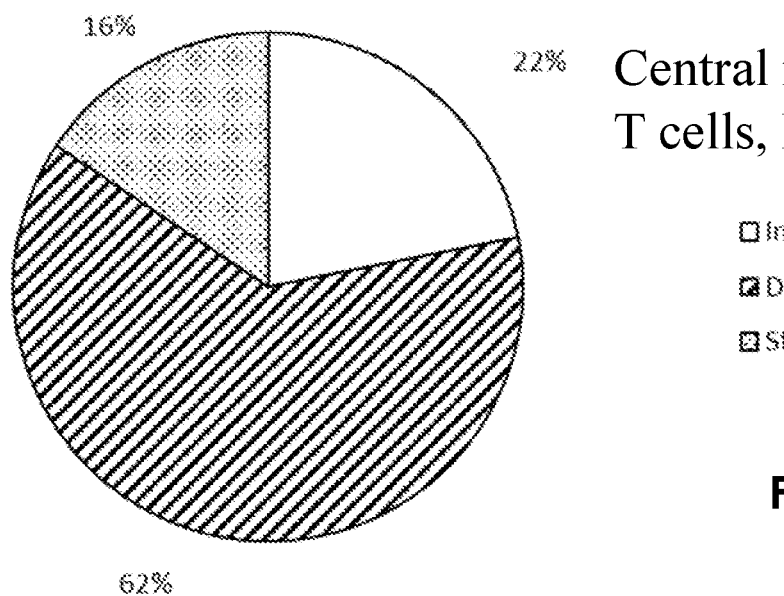

According to FIG. 6a, on day 76, 25% of individuals showed an increase (>25%) in effector T cells, according to FIG. 6b, 34% showed an increase (>25%) in effector memory T cells and according to FIG. 6c, 22% showed an increase (>25%) in central memory T cells. The increase in both effector and central memory T cell generation indicates that protective memory cell formation of the cellular immunity was established.

Figure 7A:
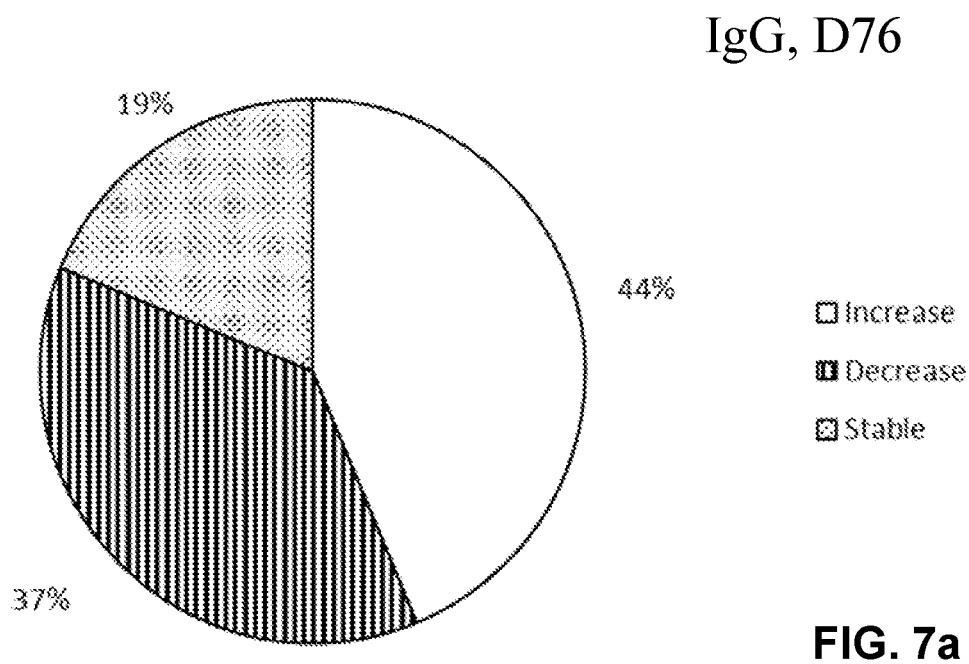
Figure 7B:
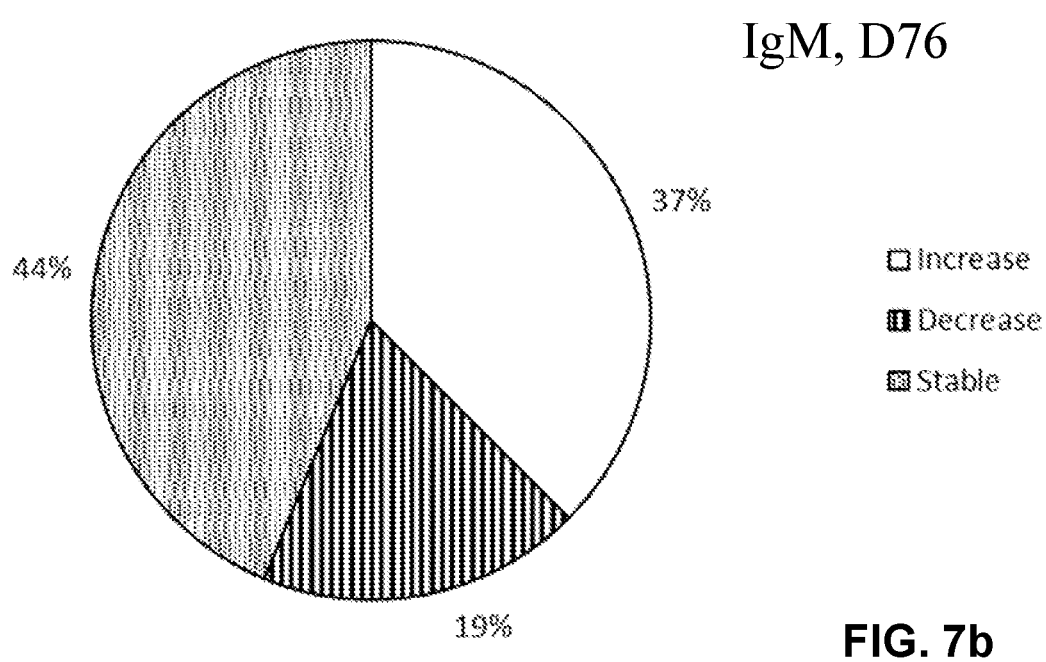

As shown in FIG. 7a, 44% of individuals showed an increase (>25%) in IgG positive cells and according to FIG. 7b, 37% showed an increase in IgM positive cells. The increase in both IgG and IgM positive cells in almost half and ⅓ of the individuals, respectively, indicates that humoral immunity was still activated.

Figure 8A:
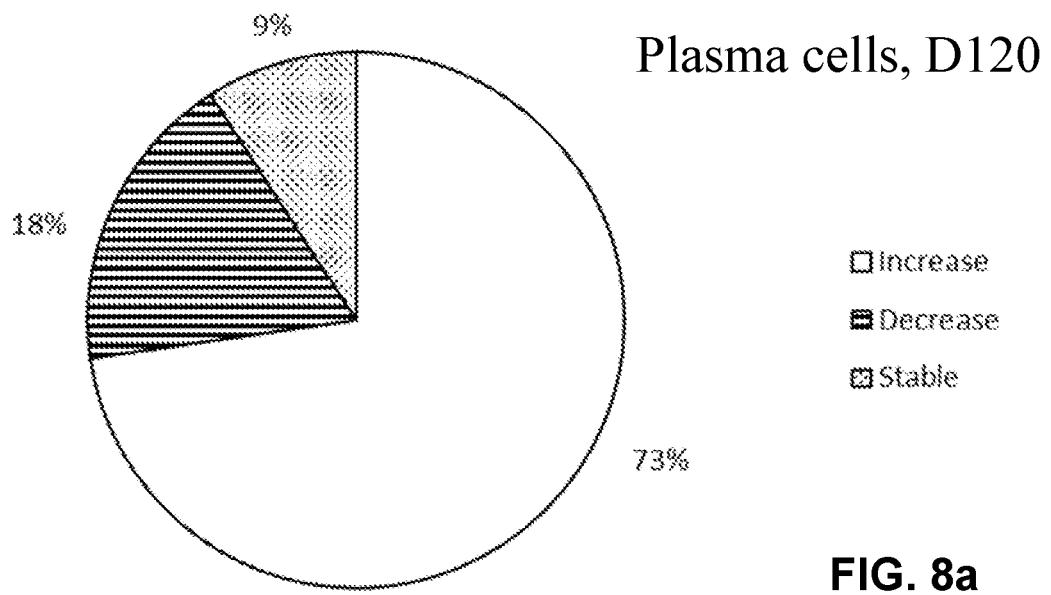
Figure 8B:
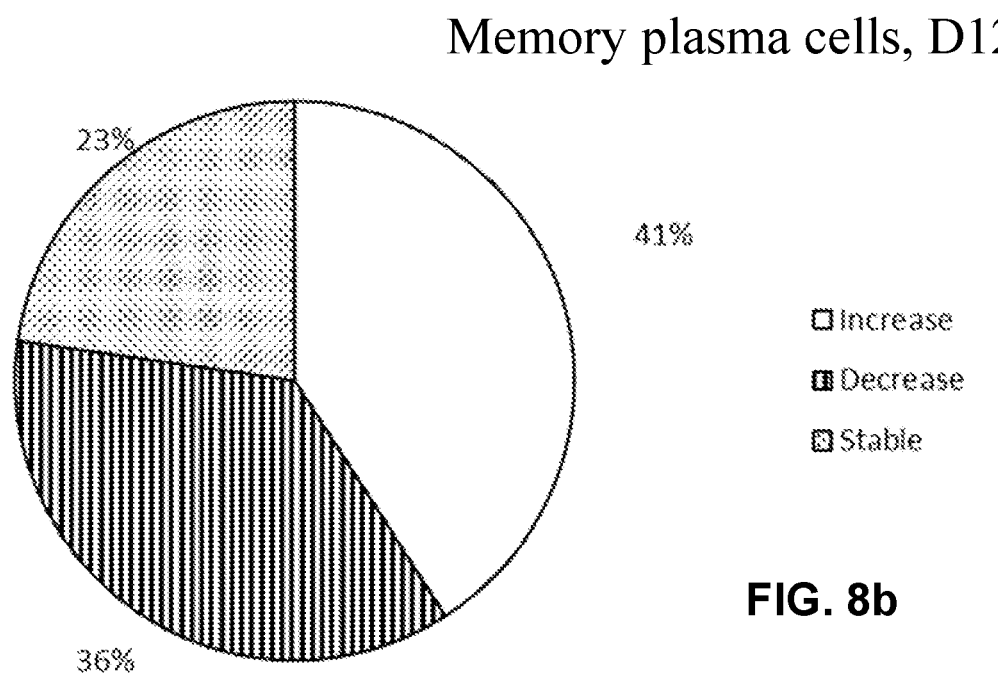

According to FIG. 8a, on day 120, 73% of individuals showed an increase (>25%) in plasma cells and, as shown in FIG. 8b, 41% showed an increase (>25%) in memory plasma cells. ⅔ of the individuals had either increased or stable plasma cells and memory plasma cells compared to day 76, indicating establishment of humoral immunity.

Figure 9A:
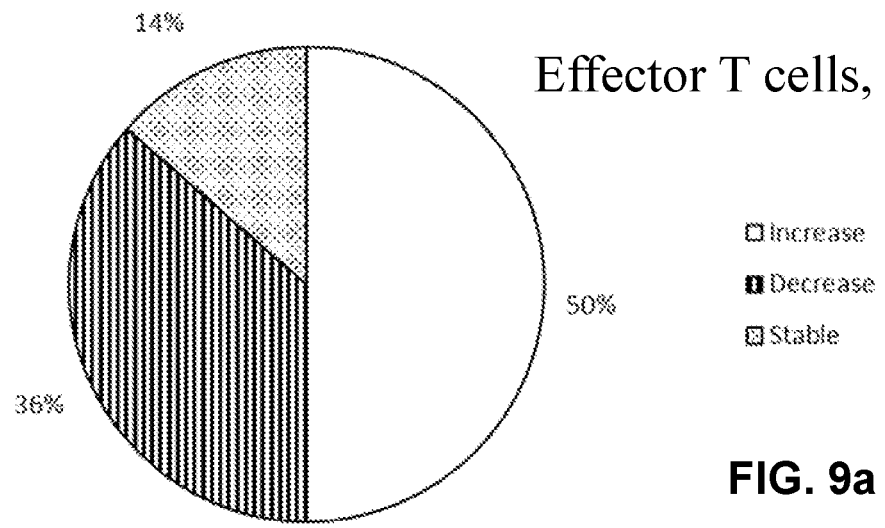
Figure 9B:
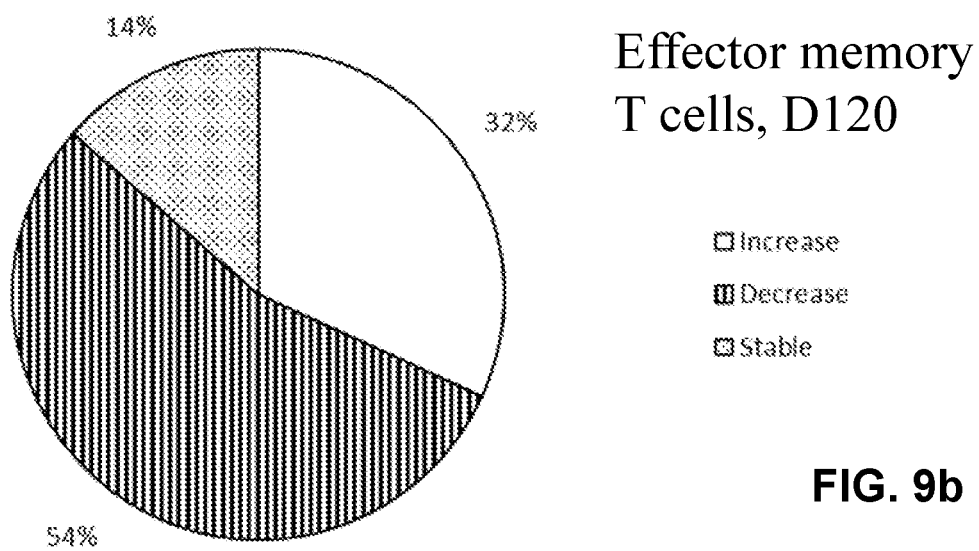
Figure 9C:
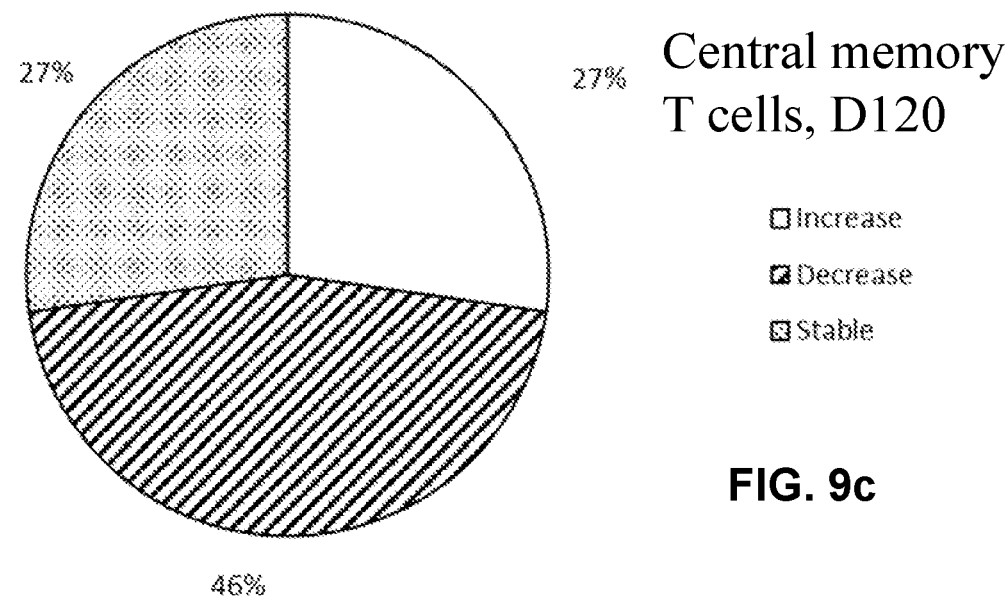

According to FIG. 9a, on day 120, 50% of individuals showed an increase (>25%) in effector T cells, according to FIG. 9b, 32% showed an increase (>25%) in effector memory T cells and according to FIG. 6c, 27% showed an increase (>25%) in central memory T cells. The increase/stabilization in both effector and effector memory T cell generation indicates that protective memory cell formation of the cellular immunity was established.

Figure 10A:
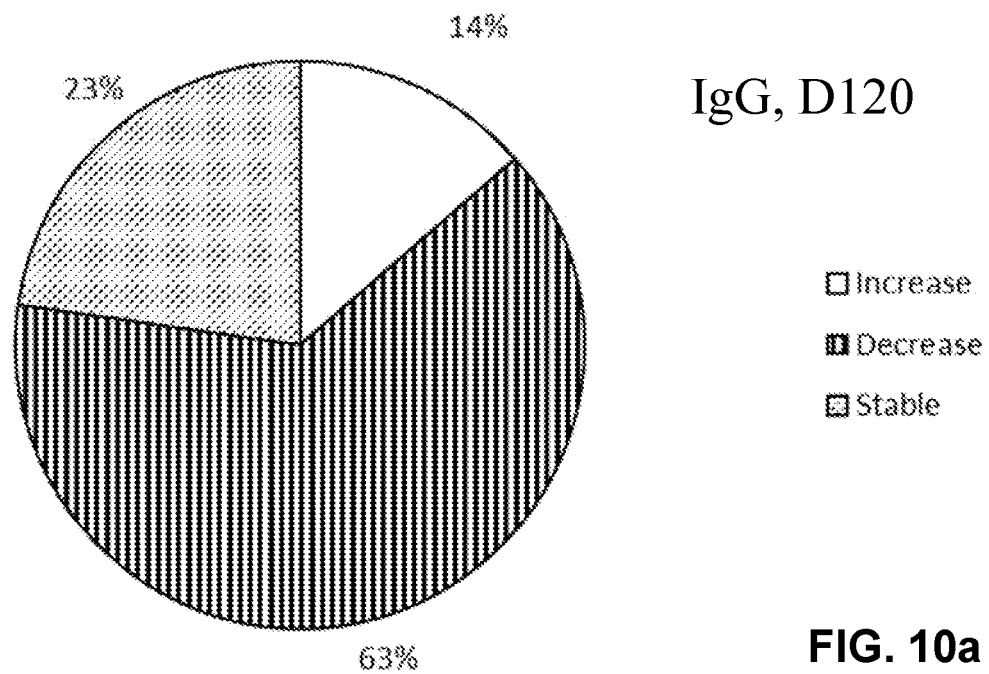
Figure 10B:
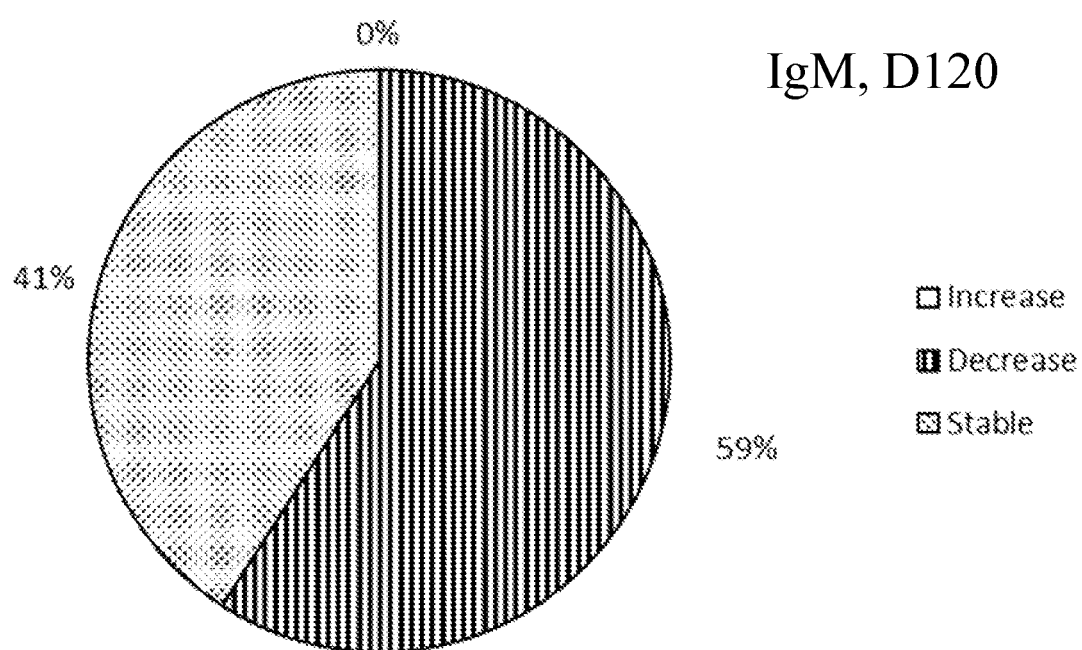

As shown in FIG. 10a, 14% of individuals showed an increase (>25%) in IgG positive cells and according to FIG. 7b, there was no further increase in IgM positive cells.

Figure 11A:
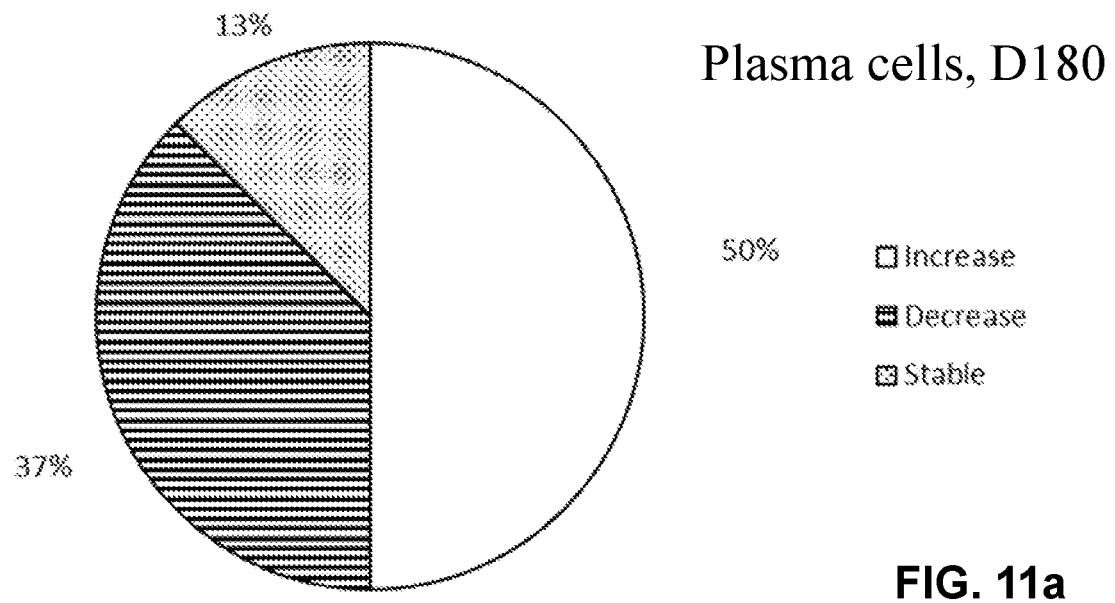
Figure 11B:
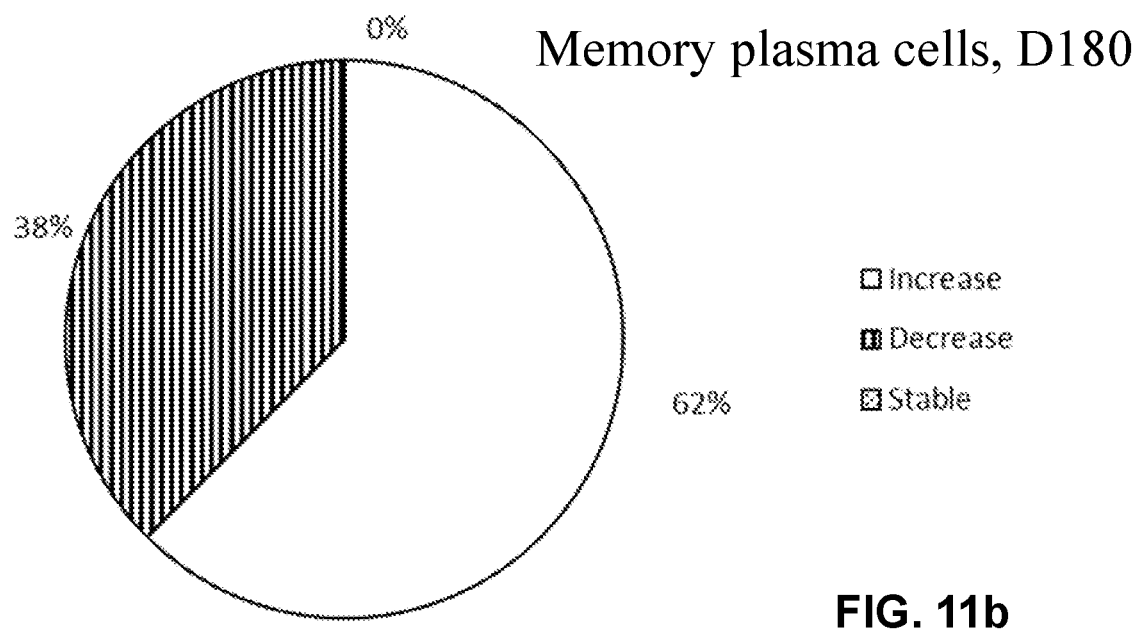

According to FIG. 11a, on day 180, 50% of individuals showed an increase (>25%) in plasma cells and, as shown in FIG. 11b, 62% showed an increase (>25%) in memory plasma cells. This indicates the establishment of humoral immunity.

Figure 12A:
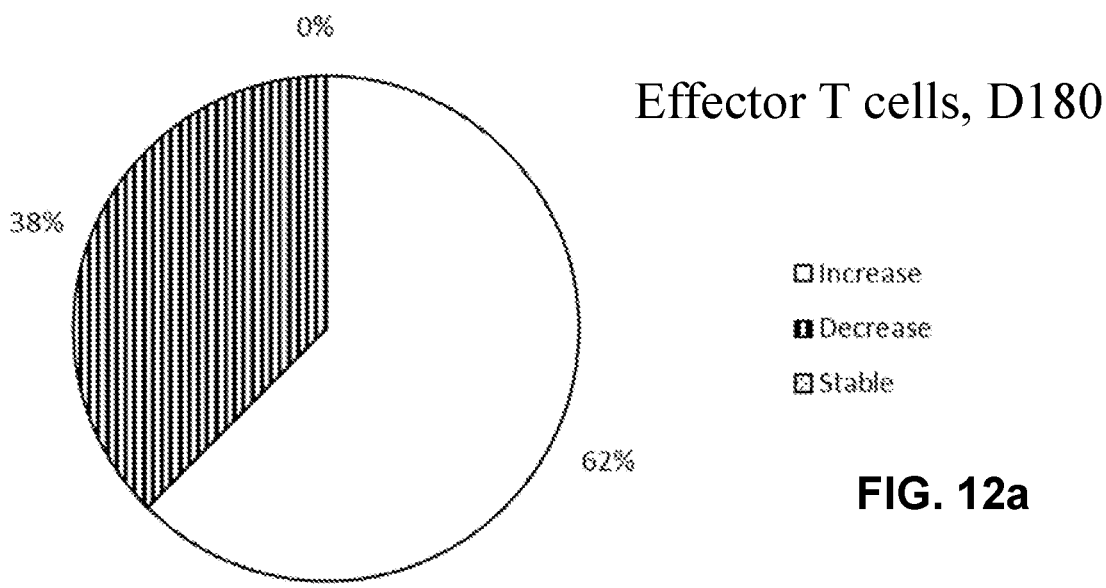
Figure 12B:
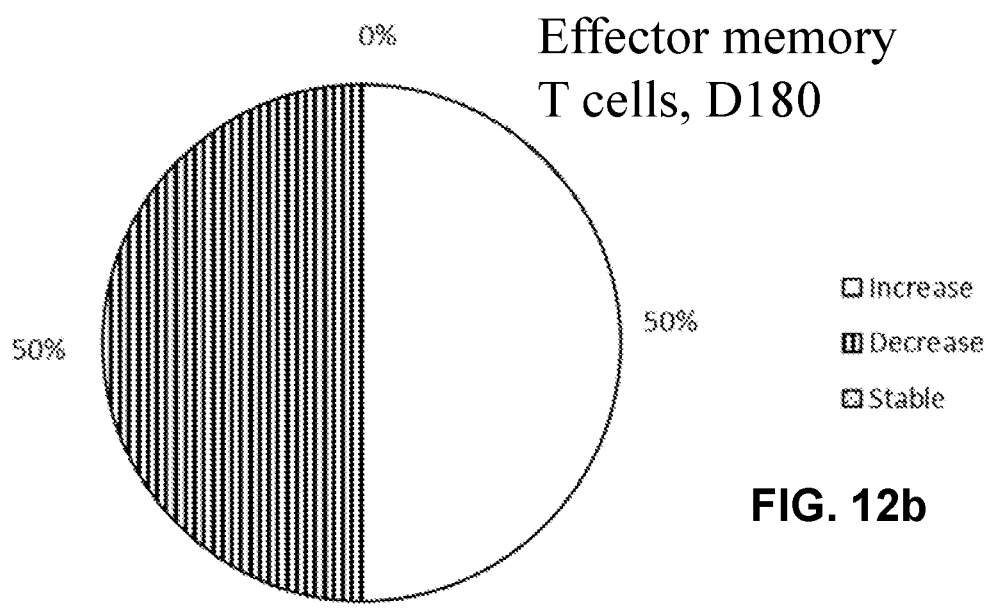
Figure 12C:
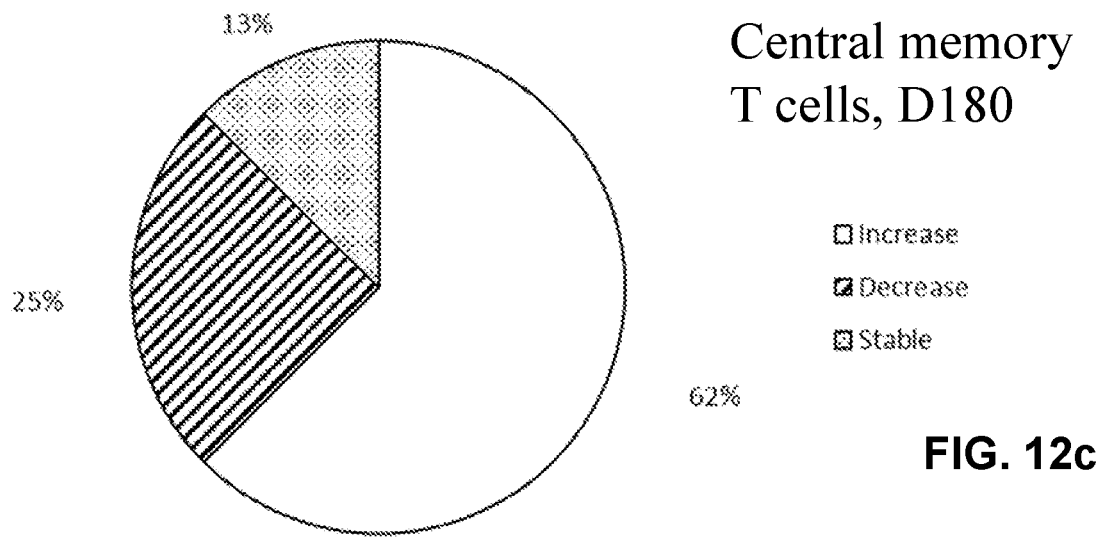

According to FIG. 12a, on day 180, 62% of individuals showed an increase (>25%) in effector T cells, according to FIG. 12b, 50% showed an increase (>25%) in effector memory T cells and according to FIG. 12c, 62% showed an increase (>25%) in central memory T cells. The increase/stabilization in both effector and effector memory T cell generation indicates that protective memory cell formation of the cellular immunity was established.

Figure 13A:
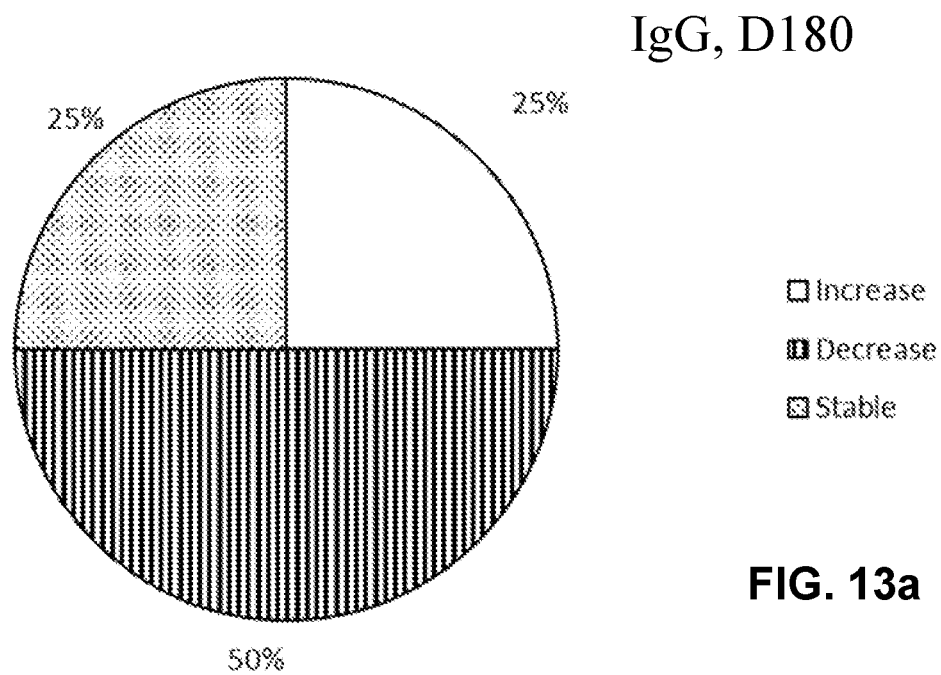
Figure 13B:
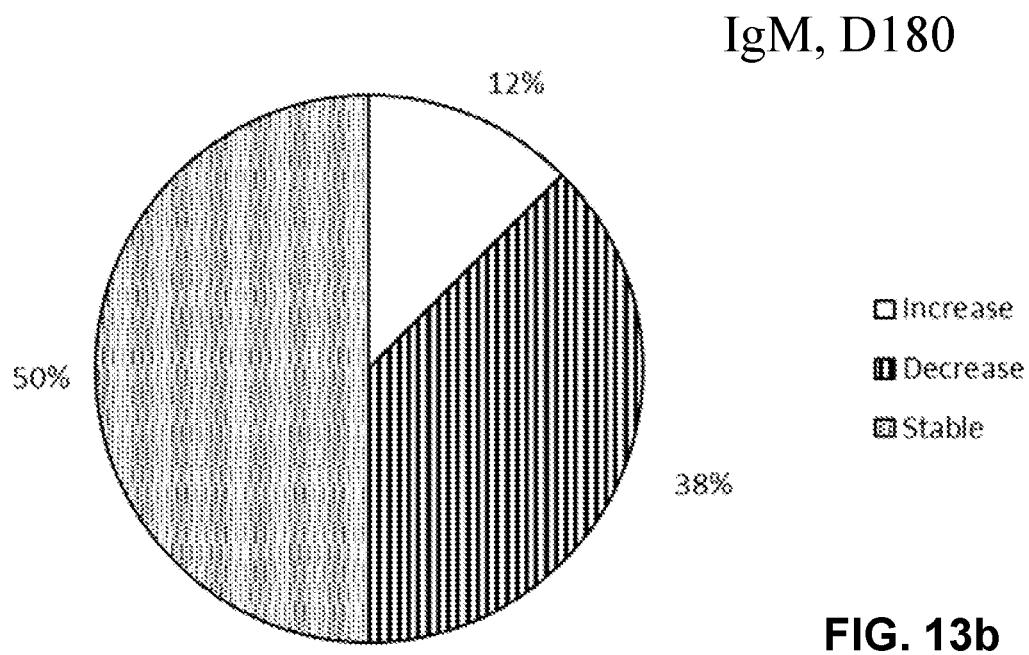

As shown in FIG. 13a, 25% of individuals showed an increase (>25%) in IgG positive cells and according to FIG. 13b, there was an increase of 12% in IgM positive cells.

The table shown in FIG. 14a indicates that on day 38, there was SARS-COV-2 specific cell mediated immunity against each of the three peptides 1-3, as determined by the secretion of IL-2. The table shown in FIG. 14b, indicates that on day 38, there was SARS-COV-2 specific cell mediated immunity against peptides 2 and 3, as determined by the secretion of IFN-gamma. The table shown in FIG. 14c, indicates that on day 38, there was SARS-COV-2 specific cell mediated immunity against each of the three peptides 1-3, as determined by the secretion of TNF-alpha.

The table shown in FIG. 15a, indicates that on day 76, there is SARS-COV-2 specific cell mediated immunity against each of the three peptides 1-3, as determined by the secretion of IL-2. The table shown in FIG. 15b, indicates that on day 76, there was SARS-COV-2 specific cell mediated immunity against peptide 3 as determined by the secretion of IFN-gamma. The table shown in FIG. 15c, indicates that on day 76, there was SARS-COV-2 specific cell mediated immunity against peptides 2 and 3, as determined by the secretion of TNF-alpha.

The tables shown in FIGS. 16a and 16b indicate that on day 120, there was no statistically increased SARS-COV-2 specific cell mediated immunity against any of the peptides, as determined by the secretion of IL-2 and IFN-gamma. The table shown in FIG. 16c, indicates that on day 120, there was SARS-COV-2 specific cell mediated immunity against peptide 2, as determined by the secretion of TNF-alpha.

The table shown in FIG. 17a, indicates that on day 180, there was SARS-COV-2 specific cell mediated immunity against each of the three peptides 1-3, as determined by the secretion of IL-2. The table shown in FIG. 17b, indicates that on day 180, there was SARS-COV-2 specific cell mediated immunity against peptides 2 and 3, as determined by the secretion of IFN-gamma. The table shown in FIG. 17c, indicates that on day 180, there was SARS-COV-2 specific cell mediated immunity against peptide 1, as determined by the secretion of TNF-alpha.

The tables shown in FIG. 18 show how specific the determination of cell mediated immunity against SARS-COV-2 is by means of IL-2, IFN-gamma and TNF-alpha measurement, respectively. The table shown in FIG. 18a indicates that none of the three peptides 1-3 caused any non-significant cell mediated immunity in non-infected volunteers according to IL-2 determination. The table shown in FIG. 18b indicates that peptides 1 and 2 did not cause any non-significant cell mediated immunity in non-infected volunteers according to IFN-g determination. Peptide 3 induced IFN-gamma secretion in non-infected individuals and therefore could not be used for the determination of SARS-COV-2 specific cell-mediated immunity. The table shown in FIG. 18c indicates that none of the three peptides 1-3 caused non significant cell mediated immunity in non-infected volunteers according to TNF-alpha determination.

The table shown in FIG. 19 shows the specificity of the immune response against the three peptides used in IST-12 preparations by the determination of CD8 positive cells, memory plasma cells and T cells activated against the three peptides. A mix of the three peptides was conjugated with Texas Red fluorescent dye. Whole blood from one SARS-COV-2 infected individual, two vaccinated individuals (one determined on day 38 and the other determined on day 180 after administration of the first dose, respectively), and two non-vaccinated, non-infected "healthy" volunteers was incubated for 2 hours with the fluorescent peptide mix. Then CLTs, plasma memory and memory T cells that recognized specifically the conjugated peptides were determined. It was found that vaccinated individuals had increased levels of plasma memory cells specific for the three peptides used. The infected individual did not have enough time to acquire humoral memory immunity. The two non-vaccinated, non-infected volunteers had very low levels of plasma memory cells specific for the three peptides used. However, the infected individual and the two vaccinated individuals had increased levels of memory T cells specific for the three peptides used, compared to the two non-vaccinated, non-infected volunteers.

The invention claimed is:

1. A pharmaceutical product, comprising:

a first composition, a second composition, and a third composition, wherein each of the first, the second, and the third compositions comprises one of three different populations of activated autologous dendritic cells from a single human or animal subject, and wherein the activated autologous dendritic cells in each of the three populations present a different peptide of a spike protein or an envelope protein of SARS-CoV-2, and each of the three peptides is selected from the group consisting of SARS-CoV-2 spike protein LPFNDGVYF peptide (SEQ ID NO: 1), SARS-CoV-2 spike protein IVRFPNITNLCPFGE peptide (SEQ ID NO: 2), SARS-CoV-2 spike protein FTISVTTEI peptide (SEQ ID NO: 3), SARS-CoV-2 spike protein YNYLYRLFRKSNLKP (SEQ ID NO: 4), SARS-CoV-2 envelope protein YSFVSEETG peptide (SEQ ID NO: 5), and SARS-CoV-2 spike protein RLNEVAKNLNESLIDL peptide (SEQ ID NO: 6).

2. The pharmaceutical product according to claim 1, wherein
the first composition comprises a first population of activated autologous dendritic cells which have been activated with a first peptide of a spike protein of SARS-CoV-2 or of an envelope protein of SARS-CoV-2,
the second composition comprises a second population of activated autologous dendritic cells which have been activated with a second peptide of a spike protein of SARS-CoV-2 or of an envelope protein of SARS-CoV-2, wherein the second peptide is different from the first peptide; and
the third composition comprises a third population of activated autologous dendritic cells which have been activated with a third peptide of a spike protein of SARS-CoV-2 or of an envelope protein of SARS-CoV-2 wherein the third peptide is different from the first peptide and the second peptide.

3. The pharmaceutical product according to claim 1, for use as a vaccine against a viral disease caused by SARS-CoV-2 in a human or animal subject.

4. The pharmaceutical product according to claim 1, for use in treatment of a viral disease caused by SARS-CoV-2, wherein the three compositions are administered to the human or animal subject separately from each other and sequentially at three different points in time, wherein the first composition is administered to the human or animal subject in week 1 of a vaccination schedule, wherein the second composition is administered to the human or animal subject in week 2 of the vaccination schedule, and wherein the third composition is administered to the human or animal subject in week 3 of the vaccination schedule.

5. A kit of parts for use as a vaccine in a human or animal subject, comprising the pharmaceutical product according to claim 1.

6. A kit of parts for use as a vaccine against a viral disease caused by SARS-CoV-2 in a human or animal subject, wherein the kit of parts comprises a first composition, a second composition and a third composition, wherein each of the first, the second, and the third compositions comprises one of three different populations of activated autologous dendritic cells from a single human or animal subject, wherein the activated autologous dendritic cells in each of the three populations present a different peptide of a spike protein of SARS-CoV-2 or an envelope protein of SARS-CoV-2, and
each of the three peptides is selected from the group consisting of SARS-CoV-2 spike protein LPFNDGVYF peptide (SEQ ID NO: 1), SARS-CoV-2 spike protein IVRFPNITNLCPFGE peptide (SEQ ID NO: 2), SARS-CoV-2 spike protein FTISVTTEI peptide (SEQ ID NO: 3), SARS-CoV-2 spike protein YNYLYRLFRKSNLKP (SEQ ID NO: 4), SARS-CoV-2 envelope protein YSFVSEETG peptide (SEQ ID NO: 5), and SARS-CoV-2 spike protein RLNEVAKNLNESLIDL peptide (SEQ ID NO: 6).

7. The kit of parts according to claim 6, wherein the kit of parts comprises a first composition, a second composition and a third composition, wherein
the first composition comprises a first population of activated autologous dendritic cells of the human or animal subject which present on their cell surface a first peptide of a spike protein of SARS-CoV-2;
the second composition comprises a second population of activated autologous dendritic cells of the human or animal subject which present on their cell surface a second peptide of a spike protein of SARS-CoV-2 different from the first peptide, or of an envelope protein of SARS-CoV-2; and
the third composition comprises a third population of activated autologous dendritic cells of the human or animal subject which present on their cell surface a third peptide of a spike protein of SARS-CoV-2 different from the first peptide and the second peptide.

8. The kit of parts according to claim 7, wherein
the first composition comprises a first population of activated autologous dendritic cells of the human or animal subject which present on their cell surface a SARS-CoV-2 spike protein LPFNDGVYF peptide (SEQ ID NO: 1); wherein
the second composition comprises a second population of activated autologous dendritic cells of the human or animal subject which present on their cell surface one peptide selected from the group consisting of SARS-CoV-2 spike protein IVRFPNITNLCPFGE peptide (SEQ ID NO: 2), SARS-CoV-2 spike protein FTISVTTEI peptide (SEQ ID NO: 3), SARS-CoV-2 spike protein YNYLYRLFRKSNLKP (SEQ ID NO: 4), and SARS-CoV-2 envelope protein YSFVSEETG peptide (SEQ ID NO: 5); and wherein
the third composition comprises a third population of activated autologous dendritic cells of the human or animal subject which present on their cell surface a SARS-CoV-2 spike protein RLNEVAKNLNESLIDL peptide (SEQ ID NO: 6).

9. The kit of parts according to claim 6, wherein the three compositions are administered to the human or animal subject separately from each other and sequentially at three different points in time.

10. The kit of parts according to claim 6, wherein the first composition is administered to the human or animal subject in week 1 of a vaccination schedule, wherein the second composition is administered to the human or animal subject in week 2 of the vaccination schedule, and wherein the third composition is administered to the human or animal subject in week 3 of the vaccination schedule.

11. A method of treating a viral disease caused by SARS-CoV-2 in a human or animal subject, comprising the followings steps:
administering the pharmaceutical product according to claim 1 to the human or animal subject, including
administration of the first composition comprising a first population of activated autologous dendritic cells of the human or animal subject which present on their cell surface a first peptide of a protein of SARS-CoV-2;
administration of the second composition comprising a second population of activated autologous dendritic cells of the human or animal subject which present on their cell surface a second peptide of a protein of SARS-CoV-2;
administration of the third composition comprising a third population of activated autologous dendritic cells of the human or animal subject which present on their cell surface a third peptide of a protein of SARS-CoV-2.

12. The method of treating a viral disease caused by SARS-CoV-2 in a human or animal subject according to claim 11, wherein
the first composition comprises a first population of activated autologous dendritic cells of the human or animal subject which present on their cell surface a first peptide of a spike protein of SARS-CoV-2; wherein
the second composition comprises a second population of activated autologous dendritic cells of the human or animal subject which present on their cell surface a second peptide of a spike protein of SARS-CoV-2 different from the first peptide, or of an envelope protein of SARS-CoV-2, and wherein
the third composition comprises a third population of activated autologous dendritic cells of the human or animal subject which present on their cell surface a third peptide of a spike protein of SARS-CoV-2 different from the first peptide and the second peptide.

13. The method of treating a viral disease caused by SARS-CoV-2 in a human or animal subject according to claim 11, wherein the first, second, and third composition are administered to the human or animal subject separately from each other and sequentially at three different points in time.

14. A method for the production of a medicament consisting of the pharmaceutical product according to claim 1, comprising the following steps:
a.) culturing monocytes isolated from peripheral blood mononuclear cells (PBMCs) of a human or animal subject;
b.) culturing adhering monocytes of step a.) with GM-CSF and IL-4, resulting in a first population of immature dendritic cells;
repeating steps a.) and b.) to obtain a second and a third population of immature dendritic cells;
c.) pulsing and incubating each of the three populations of immature dendritic cells of step b.) with a different one of three peptides of a spike protein or an envelope protein of SARS-CoV-2 selected from the group consisting of SARS-CoV-2 spike protein LPFNDGVYF peptide (SEQ ID NO: 1), SARS-CoV-2 spike protein IVRFPNITNLCPFGE peptide (SEQ ID NO: 2), SARS-CoV-2 spike protein FTISVTTEI peptide (SEQ ID NO: 3), SARS-CoV-2 spike protein YNYLYRLFRKSNLKP (SEQ ID NO: 4), SARS-CoV-2 envelope protein YSFVSEETG peptide (SEQ ID NO: 5), and SARS-CoV-2 spike protein RLNEVAKNLNESLIDL peptide (SEQ ID NO: 6), wherein in case of SARS-CoV-2 spike protein LPFNDGVYF peptide (SEQ ID NO: 1) or SARS-CoV-2 spike protein RLNEVAKNLNESLIDL peptide (SEQ ID NO: 6), the incubation is performed in the presence of β2 microglobulin, the incubation resulting in three different populations of activated autologous dendritic cells, wherein cells in each of the three populations present a different one of the three peptides of a spike protein or an envelope protein of SARS-CoV-2.

15. The pharmaceutical product according to claim 4, for use in treatment of a viral disease caused by SARS-CoV-2, wherein 50-90% of each respective composition are administered to the human or animal subject by intravenous injection and the remaining 10-50% of the respective composition are administered by subcutaneous injection.

16. The kit of parts according to claim 9, wherein the three compositions are administered to the human or animal subject by a combination of intravenous and subcutaneous injections.

17. The method of treating a viral disease caused by SARS-CoV-2 in a human or animal subject according to claim 12, wherein
the first composition comprises a first population of activated autologous dendritic cells which present on their cell surface a SARS-CoV-2 spike protein LPFNDGVYF peptide (SEQ ID NO: 1); wherein
the second composition comprises a second population of activated autologous dendritic cells which present on their cell surface one peptide selected from the group consisting of SARS-CoV-2 spike protein IVRFPNITNLCPFGE peptide (SEQ ID NO: 2), SARS-CoV-2 spike protein FTISVTTEI peptide (SEQ ID NO: 3), SARS-CoV-2 spike protein YNYLYRLFRKSNLKP (SEQ ID NO: 4), and SARS-CoV-2 envelope protein YSFVSEETG peptide (SEQ ID NO: 5); and wherein
the third composition comprises a third population of activated autologous dendritic cells which present on their cell surface a SARS-CoV-2 spike protein RLNEVAKNLNESLIDL peptide (SEQ ID NO: 6).

18. The method of treating a viral disease caused by SARS-CoV-2 in a human or animal subject according to claim 13, wherein the first composition is administered to the human or animal subject in week 1 of a vaccination schedule, the second composition is administered to the human or animal subject in week 2 of the vaccination schedule, and the third composition is administered to the human or animal subject in week 3 of the vaccination schedule.

19. The method for the production of a medicament according to claim 14, further comprising the following step:
d.) cryo-preserving the activated autologous dendritic cells until further use.

20. The method for the production of a medicament according to claim 19, further comprising, prior to step d.), the following step:
e.) maturing of the activated autologous dendritic cells presenting a peptide of a spike protein or an envelope protein of SARS-CoV-2 resulting from step c.) by incubation with a cytokine cocktail.

21. The method for the production of a medicament according to claim 20, wherein in step e.), the incubation is carried out for 48 hours at 37° C. and 5% CO2.

22. The method for the production of a medicament according to claim 14, wherein in step a.) the monocytes are isolated from PBMCs of a human or animal subject by density gradient centrifugation or by Red Blood Lysis with $NH_4Cl$ and magnetic bead isolation.

23. The method for the production of a medicament according to claim 14, wherein in step b.) the adhering monocytes of step a.) are cultured with GM-CSF and IL-4 for 6 days.

24. The method for the production of a medicament according to claim 14, wherein in step c.), each of the three populations of the immature dendritic cells of step b.) are pulsed with the respective one of the three peptides of a spike protein or an envelope protein of SARS-CoV-2 at a final concentration of 10 μg/ml.

25. The method for the production of a medicament according to claim 14, wherein in step c.), the incubation is carried out for 4-24 hours.

26. The method for the production of a medicament according to claim 14, wherein in step c.), in case of SARS-CoV-2 spike protein (84-92) LPFNDGVYF peptide (SEQ ID NO: 1) or SARS-CoV-2 spike protein (1185-1200) RLNEVAKNLNESLIDL peptide (SEQ ID NO: 6), the immature dendritic cells are incubated in the presence of β2 microglobulin at a final concentration of 3-10 μg/ml of β2 microglobulin.

27. The method for the production of a medicament according to claim 14, further comprising:
   d.) cryo-preserving the activated autologous dendritic cells until further use.

28. The method for the production of a medicament according to claim 27, further comprising, after step c.) and prior to step d.),
   e.) maturing of the activated autologous dendritic cells resulting from step c.) by incubation with a cytokine cocktail.

29. The method for the production of a medicament according to claim 28, wherein incubation with the cytokine cocktail is carried out for 48 hours at 37° C. and 5% CO2.

\* \* \* \* \*

SEQUENCE LISTING

```
<160> NUMBER OF SEQ ID NOS: 6

<210> SEQ ID NO 1
<211> LENGTH: 9
<212> TYPE: PRT
<213> ORGANISM: SARS-CoV-2

<400> SEQUENCE: 1

Leu Pro Phe Asn Asp Gly Val Tyr Phe
1               5

<210> SEQ ID NO 2
<211> LENGTH: 15
<212> TYPE: PRT
<213> ORGANISM: SARS-CoV-2

<400> SEQUENCE: 2

Ile Val Arg Phe Pro Asn Ile Thr Asn Leu Cys Pro Phe Gly Glu
1               5                   10                  15

<210> SEQ ID NO 3
<211> LENGTH: 9
<212> TYPE: PRT
<213> ORGANISM: SARS-CoV-2

<400> SEQUENCE: 3

Phe Thr Ile Ser Val Thr Thr Glu Ile
1               5

<210> SEQ ID NO 4
<211> LENGTH: 15
<212> TYPE: PRT
<213> ORGANISM: SARS-CoV-2

<400> SEQUENCE: 4

Tyr Asn Tyr Leu Tyr Arg Leu Phe Arg Lys Ser Asn Leu Lys Pro
1               5                   10                  15

<210> SEQ ID NO 5
<211> LENGTH: 9
<212> TYPE: PRT
<213> ORGANISM: SARS-CoV-2

<400> SEQUENCE: 5

Tyr Ser Phe Val Ser Glu Glu Thr Gly
1               5

<210> SEQ ID NO 6
<211> LENGTH: 16
<212> TYPE: PRT
<213> ORGANISM: SARS-CoV-2

<400> SEQUENCE: 6

Arg Leu Asn Glu Val Ala Lys Asn Leu Asn Glu Ser Leu Ile Asp Leu
1               5                   10                  15
```